United States Patent [19]

Bowers et al.

[11] Patent Number: 5,783,650
[45] Date of Patent: Jul. 21, 1998

[54] POLYMERIC SURFACE COATINGS

[75] Inventors: Roderick W. J. Bowers; Stephen A. Jones; Peter W. Stratford; Stephen A. Charles, all of Middlesex, United Kingdom

[73] Assignee: Biocompatibles Limited, Middlesex, United Kingdom

[21] Appl. No.: 478,651

[22] Filed: Jun. 7, 1995

Related U.S. Application Data

[62] Division of Ser. No. 175,348, Mar. 7, 1994, Pat. No. 5,648,442.

Foreign Application Priority Data

| Jul. 5, 1991 | [GB] | United Kingdom | 9114619 |
| Aug. 8, 1991 | [GB] | United Kingdom | 9117170 |
| Apr. 24, 1992 | [GB] | United Kingdom | 9208970 |
| Jul. 6, 1994 | [WO] | WIPO | PCT/GB92/01215 |

[51] Int. Cl.$^6$ .......... C08F 230/02; C08F 220/02; C08F 228/02; C08F 220/06
[52] U.S. Cl. .......... 526/277; 526/278; 526/287; 526/288; 526/310; 526/312; 526/320; 526/328.5; 526/332; 526/347.1
[58] Field of Search .......... 526/278, 277, 526/312, 310, 287, 288, 320, 328.5, 332, 347.1

[56] References Cited

U.S. PATENT DOCUMENTS

| 3,671,502 | 6/1972 | Samour et al. | |
| 4,111,922 | 9/1978 | Beede | 526/292 |
| 4,863,980 | 9/1989 | Cowan et al. | |
| 5,026,490 | 6/1991 | Peiffer | 252/8.51 |
| 5,045,593 | 9/1991 | Cowan | 525/54.3 |
| 5,208,295 | 5/1993 | Chaudhuri | 525/327.6 |
| 5,223,580 | 6/1993 | Chaudhuri | 525/327.6 |
| 5,270,415 | 12/1993 | Sulc | 526/265 |
| 5,461,433 | 10/1995 | Nakabayashi | 351/177 |
| 5,492,989 | 2/1996 | Chaudhuri | 526/307.6 |

FOREIGN PATENT DOCUMENTS

| 1167838 | 5/1984 | Canada . |
| 0293963 | 12/1988 | European Pat. Off. . |
| 0537972 | 4/1993 | European Pat. Off. . |
| 60-204711 | of 1985 | Japan . |
| 60-67489 | 4/1985 | Japan . |
| 60-21599 | 5/1985 | Japan . |
| 60-179408 | 9/1985 | Japan . |
| 61-205291 | 9/1986 | Japan . |
| 63-221184 | 9/1988 | Japan . |
| 1529378 | 10/1978 | United Kingdom . |
| WO9300391 | 1/1993 | WIPO . |

OTHER PUBLICATIONS

Wielema et al, Zwitterionic Polymers–I. Synthesis of a Novel Series of Poly(Vinylsulphobetaines). Effect of Structure of Polymer on Solubility in Water, *Eur. Polym. J.,* 23(12):947–950 (1987).

Ishihara et al, Protein Adsorption from Human Plasma is Reduced on Phospholipid Polymers, *17th Ann. Meet. Soc. Biomaterials,* pp. 297–298 (May, 1991).

Kojima et al, Interaction between Phospholipids and Biocompatible Polymers Containing a Phosphorylcholine Moiety, *Biomaterials,* 12:121–124 (1991).

Ishihara et al, Preparation of Phospholipid Polymers and Their Properties as Polymer Hydrogel Membranes, *Polym. J,* 22(5):355–360 (1990).

Ishihara et al, Reduced Thrombogenicity of Polymers Having Phospholipid Polar Groups, *J. Biomed. Materials Res,* 24:1069–1077 (1990).

Fukushima et al, Interaction Between the Polymer Containing Phosphorylcholine Group and Cells, *Kobunshi Ronbunshu,* 40(12)785–793 (1983).

Kadoma et al, Synthesis and Hemolysis Test of the Polymer Containing Phosphorylcholine Groups, *Kobunshi Ronbunshu,* 35(7):423–427 (1978).

Ishihara et al, "Improvement of Blood Compatibility on Cellulose Dallysis Membrane," Biomaterials, vol. 13, No. 3, 1992.

Park, SM, Journal of Korean Fibre Society (1992) 29, 32–37.

Sakurai et al, Macromolecules (1992), 25, 7256–7260.

*Primary Examiner*—Fred Zitomer
*Attorney, Agent, or Firm*—Sughrue, Mion, Zinn, Macpeak & Seas, PLLC

[57] ABSTRACT

Polymers of one or more radical polymerisable monomers which polymer has pendant groups bearing a centre of permanent positive charge and other pendant groups capable of stably binding the polymer to a surface are useful in the treatment of surfaces to render them biocompatible. The polymers may contain pendant groups which bind the polymer to a surface by physisorption, covalent bonding or ionic interactions. Additionally reactive groups in the polymer may serve as points for attachment of ligands to the polymer when coated on a surface.

12 Claims, No Drawings

POLYMERIC SURFACE COATINGS

This is a divisional of application Ser. No. 08/175,348, filed Mar. 7, 1994 now U.S. Pat. No. 5,648,442.

The present invention relates to new polymers, processes for producing them and processes for coating surfaces with them. The invention also provides improved processes for producing certain monomers and to certain new monomers used to obtain the polymers. The polymers are useful for coating surfaces of devices and materials which come into contact with protein-containing solutions and biological fluids, and rendering the surfaces bio- and haemocompatible. Surfaces may thus be rendered suitable for prolonged contact with living tissues and body fluids and with protein-containing solutions.

Materials used in the manufacture of separation substrates and devices, blood contacting devices contact and intraocular lenses, and other devices which are used in contact with protein-containing or biological fluids must be selected on the basis of acceptable physical and mechanical properties and compatibility with the protein-containing or biological fluid. For any given application of these materials it is usually difficult to optimise all of these considerations simultaneously and a compromise must be reached often resulting in less than optimal performance. For example, major biological problems are often encountered with materials which have otherwise optimal mechanical and physical properties. These problems often manifest themselves as undesirable deposition of biological components and in particular proteinaceous material. This protein adsorption results in blood clot formation in blood-contacting materials, the adsorption of tear components onto contact lenses resulting in deposit formation, formation of deposits on intraocular lenses and in separation media it results in blockage and failure of separation devices. Such effects lead to significant loss in operational performance and often complete rejection and failure of devices.

In the case of medical devices, for example prostheses and components of blood dialysis equipment, it is common practice to employ biocompatible polymers to form at least the surface of the devices to discourage protein adsorption. However, these materials are not perfect and reaction with the living tissues still remains a problem; for example surface-induced thrombosis is still a major difficulty, particularly where large quantities of blood are contacted with a foreign surface such as in artificial lungs and kidneys. Formation of a clot in an artificial organ has a number of adverse or even catastrophic effects including occlusion of the blood pathway in the extracorporeal system, or embolism if the clot breaks off the artificial surface and lodges in a host blood vessel. Dialysis membranes, heart valves, circulatory-assist devices, blood substitutes and artificial lungs all share this problem.

It is known that materials for use as biocompatible coatings should ideally:

(a) be capable of reproducible manufacture as pure materials;

(b) be capable of being coated onto surfaces without being degraded or adversely changed;

(c) have the requisite mechanical and permeability properties required for the specific function of the device for which they are intended;

(d) be sterilisable without adverse changes in, for example, permeability and mechanical or surface properties;

(e) not be damaged or degraded by the biological environment;

(f) not be carcinogenic.

In applications involving direct contact with blood further restrictions exist. Materials should not:

(g) induce significant platelet adhesion;

(h) interfere with the normal clotting mechanism; or (i) cause any significant damage to the cellular elements or soluble components of the blood.

There have been many attempts to prepare biocompatible, and specifically blood compatible (i.e. haemocompatible), surfaces, which do not activate the blood coagulation process and do not promote thrombus formation. Examples of such attempts include the preparation of negatively charged surfaces, such as by use of anionic polymers or suitably oriented electret polymers, preparation of surfaces coated with the natural anticoagulant heparin or synthetic heparin analogues, preparation of surfaces with inherently low surface free energy such as by use of silicone rubber, preparation of albumin-coated surfaces, and preparation of surfaces coated with compounds such as some polymethanes which are thought to adsorb albumin preferentially from blood. All of these however have had limitations.

We have now devised new film-forming polymers which can be used to coat surfaces. It has been found that these copolymers may be used to provide stable coatings on a wide variety of surfaces including, polyethylene, PVC, steel and poly(imide). The invention also provides physiadsorbable polymers which when used to coat surfaces, do not swell, to any significant extent, in aqueous environments; in some situations swelling in aqueous environments can reduce the stability of coatings of physiadsorbable polymers on surfaces.

The polymers which contain zwitterionic groups, mimic the zwitterionic structure of phospholipids such as phosphatidylcholine and sphingomyelin which are the major components of the outer membrane of all living cells. In this way the present invention seeks to provide a biocompatible surface on a coated substrate at which the deposition of proteins and cells at the substrate is minimised when the coated substrate comes into contact with a protein-containing solution or biological fluid.

In addition a variety of ligands may be attached to the polymers of the present invention when coated onto a substrate. Alternatively ligands may be attached to the polymers prior to coating on a substrate, e.g. when the polymer is in solution. The polymers of the present invention may therefore provide a means of attachment of such ligands. The term ligand includes, but is not limited to, specific binding agents such as immunoglobulins and associated fragments thereof such as those useful for affinity separation and diagnostic applications, photosensitive and chemisensitive moieties such as those useful for detector and sensor applications and therapeutic agents useful for clinical applications. Other ligands include peptide fragments which may be chemically linked to a polymer of the invention, such as fragments which induce cell attachment and may therefore be used to allow the polymers of the present invention to provide cell seeding.

The present invention provides a polymer of one or more radical polymerisable, preferably ethylenically unsaturated, monomers, which polymer has pendant groups bearing a centre of permanent positive charge and other pendant groups capable of stably binding the polymer to a surface. Such coatings bind to surfaces with good adhesion and are not removable in the environment in which the coated surfaces are used, e.g. in use as a coating on a blood-contacting surface.

Groups bearing a centre of permanent positive charge can be cationic but are most preferably zwitterionic. Such zwitterionic groups mimic the structure of the head groups of phospholipids in cells. Without wishing to be limited by this theory, it is thought that the presence of such groups at a surface renders the surface more biocompatible.

The extent to which a polymer renders a surface biocompatible may be assessed as a combination of factors such as reduction in the extent to which the surface causes blood platelet activation, protein adsorption, (for instance as judged by absorption of fibrinogen from human plasma) and reaction with C-reactive protein which is caused by the presence on the surface of isolated zwitterionic, e.g. phosphate ammonium ester groups. Preferably the polymers of the invention when coated onto a substrate, provide a reduction in platelet activation of at least 70%, more preferably at least 90%, as assessed by the assay described hereinafter compared to an untreated substrate. It is also preferred that the polymers of the invention, when coated onto a substrate, provide a reduction in fibrinogen absorption of at least 60% as assessed by the assay described hereinafter and a protein index of less than $1.5 \times 10^{-3}$ compared to an untreated substrate. The protein index is defined as the ratio of the absorbance due to C-reactive protein measured in the assay described hereinafter to the reduction in fibrinogen adsorption.

The nature of the groups capable of binding the polymer to a surface will be selected depending upon the nature of the surface which it is intended to coat with the polymer. Where the surface is hydrophobic, groups capable of being physisorbed at the surface may be used to bind the polymer to the surface. Where the surface is hydrophilic and bears functional groups then groups which are capable of reacting with surface functional groups to form covalent bonds may be used to bind the polymer to the surface. Where the surface is charged then groups bearing ionic charge may be used to bind the polymer to the surface by ionic interactions.

Polymers of the invention may therefore bind to a surface by physisorption, covalent or ionic bonding depending upon the precise nature of the surface. In certain cases it may be possible to use two of these binding mechanisms in combination.

The groups capable of stably binding the polymer to a surface may be present in the same monomer as the groups bearing a centre of permanent positive charge, or they may be in separate monomer species which are copolymerised to provide the polymer of the invention.

It will be understood that throughout, where a group is referred to as capable of binding a polymer to a surface this is intended to mean stably binding.

Where a hydrophobic surface is to be coated, alkyl groups of 6 or more carbon atoms, or fluoroalkyl groups, optionally having one or more etheric oxygen atoms interrupting the carbon chain, and optionally containing one or more carbon-carbon double or triple bonds, or siloxane groups, preferably containing from 1 to 50, more preferably 5 to 30, silicon atoms, may be used as the pendant groups capable of binding the polymer to a surface. Such groups are capable of forming strong secondary valence interactions with a surface, and being physisorbed at a hydrophobic surface, i.e. adsorbed without formation of a covalent interaction.

In one embodiment the present invention therefore provides a polymer obtainable by (i) copolymerising a radical polymerisable, preferably an ethylenically unsaturated, comonomer containing a group bearing a centre of permanent positive charge, which is preferably zwitterionic, and a radical polymerisable, preferably an ethylenically unsaturated, comonomer containing a radical polymerisable moiety and an alkyl group of 6 or more carbon atoms, which alkyl group optionally contains one or more etheric oxygen atoms and optionally one or more carbon-carbon double or triple bonds, or a fluoroalkyl group which optionally contains one or more etheric oxygen atoms and optionally one or more carbon-carbon double or triple bonds, or a siloxane group; or (ii) polymerising a radical polymerisable, preferably ethylenically unsaturated, monomer containing a group bearing a centre of permanent positive charge which is preferably zwitterionic, and an alkyl group of 6 or more carbon atoms, which alkyl group optionally contains one or more etheric oxygen atoms, or a fluoroalkyl group which optionally contains one or more etheric oxygen atoms, or a siloxane group.

Such a polymer may be a copolymer comprising residues of a radical polymerisable, preferably ethylenically unsaturated, comonomer containing a group bearing a centre of permanent positive charge and of a radical polymerisable, preferably ethylenically unsaturated comonomer containing, in addition to the radical polymerisable moiety, an alkyl group of 6 or more carbon atoms which group optionally contains one or more etheric oxygen atoms and optionally one or more carbon-carbon double or triple bonds or a fluoroalkyl group which optionally contains one or more etheric oxygen atoms and optionally one or more carbon-carbon double or triple bonds, or a siloxane group.

Alternatively such a polymer may comprise or consist of residues of a radical polymerisable, preferably ethylenically unsaturated, monomer containing a group bearing a centre of permanent positive charge and an alkyl group of 6 or more carbon atoms which group optionally contains one or more etheric oxygen atoms or a fluoroalkyl group which optionally contains one or more etheric oxygen atoms, or a siloxane group.

In this embodiment, preferably the polymer is a copolymer comprising residues of a comonomer containing a physisorbable group and a comonomer containing a group bearing a centre of permanent positive charge.

It is also preferred that the physisorbable group is an alkyl or fluoroalkyl group optionally containing one or more carbon-carbon double or triple bonds. Such a group may contain one or more etheric oxygen atoms, but in an especially preferred embodiment does not contain any etheric oxygen atoms.

In one embodiment, where the physisorbable group is an alkyl or fluoroalkyl group, optionally containing one or more etheric oxygen atoms, this group does not contain any carbon-carbon double or triple bonds.

Where a hydrophilic surface having functional groups is to be coated, groups capable of covalently binding the polymer to the surface may be incorporated into the polymer as pendant groups.

Thus according to an alternative embodiment, the invention provides a polymer obtainable by:

(i) copolymerising a radical polymerisable, preferably ethylenically unsaturated, comonomer containing a group bearing a centre of permanent positive charge, which is preferably zwitterionic, and a radical polymerisable, preferably ethylenically unsaturated, comonomer bearing a reactive group capable of covalently binding the polymer to a surface; or (ii) polymerising a radical polymerisable, preferably ethylenically unsaturated, monomer containing a group bearing a centre of permanent positive charge, which is preferably zwitterionic, and a reactive group capable of covalently binding the polymer to a surface.

Such a polymer may be a copolymer comprising residues of a radical polymerisable, preferably ethylenically unsaturated, comonomer containing a group bearing a centre of permanent positive charge and a radical polymerisable, preferably ethylenically unsaturated, comonomer bearing a reactive group and is capable of covalently binding to a surface.

Alternatively, such a polymer may comprise or consist of residues of a radical polymerisable, preferably ethylenically unsaturated, monomer containing a group bearing a centre of permanent positive charge and a reactive group capable of covalently binding to a surface.

In this embodiment, preferably the polymer is a copolymer comprising residues of a comonomer containing a group bearing a centre of permanent positive charge and a comonomer containing a reactive group capable of covalently binding to the surface.

Where a surface bearing an ionic charge is to be coated, ionic groups, capable of binding the polymer to the surface by ionic interactions, may be incorporated into the polymer of the invention as pendant groups.

According to a third embodiment, the invention therefore provides a polymer obtainable by:

(i) copolymerising a radical polymerisable, preferably ethylenically unsaturated, comonomer containing a group bearing a centre of permanent positive charge which is preferably zwitterionic, and a radical polymerisable, preferably ethylenically unsaturated, comonomer bearing an ionic group capable of binding to a surface by ionic interaction; or (ii) polymerising a radical polymerisable, preferably ethylenically unsaturated, monomer containing a group bearing a centre of permanent positive charge, which is preferably zwitterionic, and an ionic group capable of binding to a surface by ionic interaction.

Such a polymer may be a copolymer comprising residues of a radical polymerisable, preferably ethylenically unsaturated, comonomer containing a group bearing a centre of permanent positive charge, and residues of a comonomer containing an ionic group capable of binding to a surface by ionic interaction.

Alternatively such a polymer may comprise or consist of residues of a radical polymerisable, preferably ethylenically unsaturated, monomer containing a group bearing a centre of permanent positive charge and an ionic group capable of binding to a surface by ionic interaction.

In this embodiment, preferably the polymer is a copolymer comprising residues of a comonomer containing a group bearing a centre of permanent positive charge and residues of a comonomer containing an ionic group capable of binding to a surface by ionic interaction.

Optionally, in any of the above embodiments, the polymers also comprise residues of one or more diluent and/or crosslinkable monomers.

The invention also provides a process for producing such a polymer which comprises polymerising such monomers and a process for coating a surface with such a polymer, for instance a process comprising the steps of (a) polymerising such monomers to form the polymer and (b) coating the surface with the polymer so formed. Optionally, the process further comprises attaching a ligand to the polymer either in solution before coating the surface, or, more preferably when coated on the surface.

In a specific embodiment the invention further provides such polymers containing residues of a crosslinkable monomer, which are uncrosslinked, when either coated on a surface or not coated on a surface and such polymers which are crosslinked when coated on a surface. The invention further provides a process of crosslinking such polymers when coated on a surface.

As yet a further feature, the present invention provides certain new monomers useful in producing the polymers of the invention.

Monomers and comonomers which may be used in the polymers of the invention will now be described in more detail.

It is to be understood that throughout the specification (alk)acrylate, (alk)acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

Monomers Bearing A Centre of Permanent Positive Charge.

The monomer (or comonomer) bearing the centre of permanent positive charge can either be cationic or, more preferably zwitterionic. In the latter case the monomer includes within its structure not only a centre of permanent positive charge but also a centre of negative charge. Typically the centre of permanent positive charge is provided by a quaternary nitrogen atom.

Preferred comonomers which bear a centre of positive charge are of general formula (I)

$$Y-B-X \qquad (I)$$

wherein B is a straight or branched alkylene, oxaalkylene or oligo-oxaalkylene chain optionally containing one or more fluorine atoms up to and including perfluorinated chains or, if X contains a carbon-carbon chain between B and the centre of permanent positive charge or if Y contains a terminal carbon atom bonded to B, a valence bond;

X is a group bearing a centre of permanent positive charge, preferably a zwitterionic group and Y is an ethylenically unsaturated polymerisable group selected from $$CH_2=C\underset{\underset{O}{\|}}{\overset{\overset{R}{|}}{C}}-C-A- \quad \text{or} \quad \text{(styryl)}\!-\!K-$$

wherein:

R is hydrogen or a $C_1$–$C_4$ alkyl group;

A is —O— or —$NR^1$— where $R^1$ is hydrogen or a $C_1$–$C_4$ alkyl group or $R^1$ is —B—X where B and X are as defined above; and K is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$—, —$(CH_2)_pNR^2C(O)NR^2$—, (in which the groups $R^2$ are the same or different) —$(CH_2)_pO$—, —$(CH_2)_pSO_3$—, or, optionally in combination with B, a valence bond and p is from 1 to 12 and $R^2$ is hydrogen or a $C_1$–$C_4$ alkyl group.

The proviso on whether B may be a valence bond ensures that the centre of permanent positive charge in X is not directly bonded to a heteroatom, such as an oxygen or nitrogen atom in Y.

Preferred monomers containing a group bearing a centre of permanent positive charge are therefore of general formula (II) or (III).

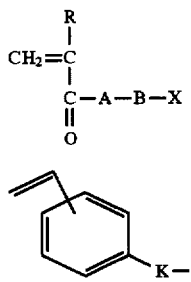

where R, A, B, K and X are as defined with reference to formula (I).

Preferably in the compounds of formula (II) R is hydrogen, methyl, or ethyl, more preferably methyl, so that (II) is an acrylic acid, methacrylic acid or ethacrylic acid derivative.

In the compounds of formula (III) K may be a valence bond and B a group, K may be a group and B a valence bond, both K and B may be groups, or K and B may together be a valence bond. Preferably B is a group where K is a valence bond.

Where K is a group then preferably p is from 1 to 6, more preferably 1,2 or 3 and most preferably p is 1. When K is a group —$(CH_2)_pNR^2$—, —$(CH_2)_pNR^2C(O)$—, —$(CH_2)_pC(O)NR^2$, —$(CH_2)_pNR^2C(O)O$—, —$(CH_2)_pOC(O)NR^2$— or —$(CH_2)_pNR^2C(O)NR2$— then $R^2$ is preferably hydrogen, methyl or ethyl, more preferably hydrogen.

In the compounds of formula (III) preferably the vinyl group is para to the group —K—B—X.

Preferably B is:

- an alkylene group of formula —$(CR^3_2)_a$—, wherein the groups —$(CR^3_2)$— are the same or different, and in each group —$(CR^3_2)$— the groups $R^3$ are the same or different and each group $R^3$ is hydrogen, fluorine or $C_{1-4}$ alkyl or fluroalkyl, preferably hydrogen, and a is from 1 to 12, preferably 1 to 6;
- an oxaalkylene group such as alkoxyalkyl having 1 to 6 carbon atoms in each alkyl moiety, more preferably —$CH_2O(CH_2)_4$—; or
- an oligo-oxaalkylene group of formula —$[(CR^4_2)_bO]_c(CR^4_2)_b$— where the groups —$(CR^4_2)$— are the same or different and in each group —$(CR^4_2)$— the groups $R^4$ are the same or different and each group $R^4$ is hydrogen, fluorine or $C_{1-4}$ alkyl or fluoroalkyl, preferably hydrogen, and b is from 1 to 6, preferably 2 or 3 and c is from 2 to 11, preferably 2 to 5; or
- if X contains a carbon-carbon chain between B and the centre of permanent positive charge or if Y contains a terminal carbon atom, a valence bond.

Preferred groups B include alkylene, oxaalkylene and oligo-oxaalkylene groups of up to 12 carbon atoms optionally containing one or more fluorine atoms. Where the polymer is not intended for coating a hydrophobic surface, and therefore is not intended to be bound by physiosorption to a surface, then preferably B is an alkylene, oxaalkylene or oligo-oxaalkylene group which does not contain any fluorine atoms.

In compounds of formula (III) it is preferred that K and B contain up to 12 carbon atoms in total.

Preferred groups X containing a centre of permanent positive charge, are the groups of formula (IVA), (IVB), (IVC), (IVD), (IVE) and (IVF) as defined below: monomers containing such groups may be used in combination with further monomers containing groups capable of binding to a surface, to provide a copolymer of the invention. Of these groups of formula (IVB)–(IVF) and especially (IVC) are particularly preferred.

In addition, groups of formula (VA), (VB) and (VC) are preferred as monomers containing both a centre of permanent positive charge and an alkyl, fluoroalkyl or siloxane group capable of binding to a surface by physisorption.

The groups of formula (IVA) are:

where the groups $R^5$ are the same or different and each is hydrogen or $C_{1-4}$ alkyl and Z is a counter ion.

Preferably the groups $R^5$ are all the same. It is also preferable that at least one of the groups $R^5$ is methyl, and more preferable that all the groups $R^5$ are methyl.

The counterion Z present in the compounds of formula (II) or (III) containing a group of formula (IVA) is such that the compounds are neutral salts. The counterion may be exchanged with ions in physiological fluids and thus the specific nature of the counterion is not critical in the present invention. However, physiologically acceptable counterions are preferred. Suitable physiologically acceptable counterions include halide anions, such as chloride or bromide ions, other inorganic anions such as sulphate, phosphate and phosphite and organic anions such as aliphatic mono-, di- or tri-carboxylate anions containing from 2 to 25 carbons atoms and optionally bearing one or more hydroxyl groups e.g. acetate, citrate and lactate.

When X is a group of formula (IVA), preferably B is a group of formula —$(CR^3_2)$— or —$(CR^3_2)_2$—, eg. —$(CH_2)$— or —$(CH_2CH_2)$—.

The groups of formula (IVB) are:

where the groups $R^6$ are the same or different and each is hydrogen or $C_{1-4}$ alkyl and d is from 2 to 4.

Preferably the groups $R^6$ are the same. It is also preferable that at least one of the groups $R^6$ is methyl, and more preferable that the groups $R^6$ are both methyl.

Preferably d is 2 or 3, more preferably 3.

When X is a group of formula (IVB) preferably B is a group of formula —$(CR^3_2)$— or —$(CR^3_2)_2$—, eg. —$(CH_2)$— or —$(CH_2CH_2)$—.

The groups of formula (IVC) are:

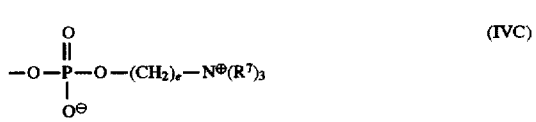

where the groups $R^7$ are the same or different and each is hydrogen or $C_{1-4}$ alkyl, and e is from 1 to 4.

Preferably the groups $R^7$ are the same. It is also preferable that at least one of the groups $R^7$ is methyl, and more preferable that the groups $R^7$ are all methyl.

Preferably e is 2 or 3, more preferably 2.

When X is a group of formula (IVC) preferably B is a group of formula —$(CR^3_2)$— or —$(CR^3_2)_2$—, eg. —$(CH_2)$— or —$(CH_2CH_2)$—.

The groups of formula (IVD) are:

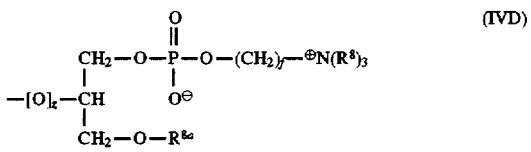

wherein the groups $R^8$ are the same or different and each is hydrogen or $C_{1-4}$ alkyl, $R^{8a}$ is hydrogen or, more preferably, a group $—C(O)B^1IR^{8b}$ where $R^{8b}$ is hydrogen or methyl, preferably methyl, $B^1$ is a valence bond or straight or branched alkylene, oxaalkylene or oligo-oxaalkalyene group, and f is from 1 to 4; and if B is other than a valence bond Z is 1 and if B is a valence bond Z is O, if X is directly bonded to an oxygen or nitrogen atom and otherwise Z is 1.

Preferably the groups $R^8$ are the same. It is also preferable that at least one of the groups $R^8$ is methyl, and more preferable that the groups $R^8$ are all methyl.

Preferably f is 1 or 2, more preferably 2.

Preferably $B^1$ is:

a valence bond;

an alkylene group of formula $—(CR^{3a}_2)_{aa}—$, wherein the groups $—(CR^{3a}_2)—$ are the same or different, and in each group $—(CR^{3a}_2)—$ the groups $R^{3a}$ are the same or different and each group $R^{3a}$ is hydrogen or $C_{1-4}$ alkyl, preferably hydrogen, and aa is from 1 to 12, preferably 1 to 6;

an oxaalkylene group such as alkoxyalkyl having 1 to 6 carbon atoms in each alkyl moiety, more preferably $—CH_2O(CH_2)_4—$; or an oligo-oxaalkylene group of formula $—[(CR^{4a}_2)_{ba}O]_{ca}—$ where the groups $—(CR_{4a2})—$ are the same or different and in each group $—(CR^{4a}_2)—$ the groups $R^{4a}$ are the same or different and each group $R^{4a}$ is hydrogen or $C_{1-4}$ alkyl, preferably hydrogen, and ba is from 1 to 6, preferably 2 or 3, and ca is from 1 to 12, preferably 1 to 6.

Preferred groups $B^1$ include a valence bond and alkylene, oxaalkylene and oligo-oxaalkylene groups of up to 12 carbon atoms.

Preferably B and $B^1$ are the same.

When X is a group of formula (IVD) preferably B is a group of formula $—[(CR^4_2CR^4_2)_cO_b]CR^4_2CR^4_2—$, eg. $—(CH_2CH_2O)_c(CH_2CH_2)—$.

The groups of formula (IVE) are:

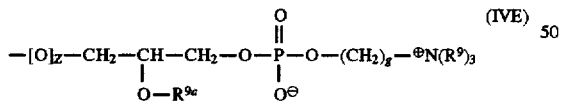

wherein the groups $R^9$ are the same or different and each is hydrogen or $C_1$-$CH_4$ alkyl, $R^{9a}$ is a hydrogen or, more preferably, a group $—C(O)B^2R^{9b}$, $R^{9b}$ is hydrogen or methyl, preferably methyl, $B^2$ is a valence bond or a straight or branched alkylene, oxaalkylene or oligo-oxaalkylene group, and g is from 1 to 4; and if B is other than a valence bond Z is 1 and if B is a valence bond Z is O if X is directly bonded to an oxygen or nitrogen atom and otherwise Z is 1.

Preferably the groups $R^9$ are the same. It is also preferable that at least one of the groups $R^9$ is methyl, and more preferable that the groups $R^9$ are all methyl.

Preferably g is 1 or 2, more preferably 2.

Preferably $B^2$ is:

a valence bond;

an alkylene group of formula $—(CR^{3b}_2)_{ab}—$, wherein the groups $—(CR^{3b}_2)—$ are the same or different, and in each group $—(CR^{3b}_2)—$ the groups $R^{3b}$ are the same of different and each group $R^{3b}$ is hydrogen or $C_{1-4}$ alkyl, preferably hydrogen, and ab is from 1 to 12, preferably 1 to 6;

an oxaalkylene group such as alkoxyalkyl having 1 to 6, carbon atoms in each alkyl moiety, more preferably $—CH_2O(CH_2)_4—$; or an oligo-oxaalkylene group of formula $—[(CR^{4b}_2)_{bb}O]_{cb}—$ where the groups $—(CR^{4b}_2)—$ are the same or different and in each group $—(CR^{4b}_2)—$ the groups $R^{4b}$ are the same or different and each group $R^{4b}$ is hydrogen or $C_{1-4}$ alkyl, preferably hydrogen, and bb is from 1 to 6, preferably 2 or 3, and cb is from 1 to 12, preferably 1 to 6.

Preferred groups $B^2$ include a valence bond and alkylene, oxalkylene and oligo-oxalkylene groups of up to 12 carbon atoms.

Preferably B and $B^2$ are the same.

When X is a group of formula (IVE) preferably B is a group of formula $—[(CR^4_2CR^4_2)_bO]_cCR^4_2CR^4_2—$, eg. $—(CH_2CH_2O)_cCH_2CH_2—$.

The groups of formula (IVF) are:

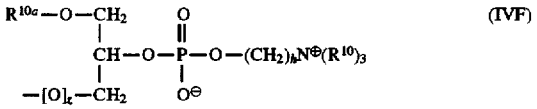

wherein the groups $R^{10}$ are the same or different and each is hydrogen or $C_{1-4}$ alkyl, $R^{10a}$ is hydrogen or, more preferably, a group $—C(O)B^3R^{10b}$ where $R^{10b}$ is hydrogen or methyl, preferably methyl, $B^3$ is a valence bond or a straight or branched alkylene, oxaalkylene or oligo-oxaalkylene group, and h is from 1 to 4; and if B is other than a valence bond Z is 1 and if B is a valence bond Z is 0 if X is directly bonded to the oxygen or nitrogen and otherwise Z is 1.

Preferably the groups $R^{10}$ are the same. It is also preferable that at least one of the groups $R^{10}$ is methyl, and more preferable that the groups $R^{10}$ are all methyl.

Preferably h is 1 or 2, more preferably 2.

Preferably $B^3$ is:

a valence bond;

an alkylene group of formula $—(CR^{3c}_2)_{ac}—$, wherein the groups $—(CR^{3c}_2)—$ are the same or different, and in each group $—(CR^{3c}_2)—$ the groups $R^{3c}$ are the same or different and each group $R^{3c}$ is hydrogen or $C_{1-4}$ alkyl, preferably hydrogen, and ac is from 1 to 12, preferably 1 to 6;

an oxaalkylene group such as alkoxyalkyl having 1 to 6 carbon atoms in each alkyl moiety, more preferably $—CH_2O(CH_2)_4—$; or an oligo-oxaalkylene group of formula $—[(CR^{4c}_2)_{bc}O]_{cc}—$ where the groups $—(CR^{4c}_2)—$ are the same or different and in each group $—(CR^{4c}_2)—$ the groups $R^{4c}$ are the same or different and each group $R^{4c}$ is hydrogen or $C_{1-4}$ alkyl, preferably hydrogen, and bc is from 1 to 6, preferably 2 or 3, and cc is from 1 to 12, preferably 1 to 6.

Preferred groups $B^3$ include a valence bond and alkylene, oxaalkylene and oligo-oxaalkylene groups of up to 12 carbon atoms.

Preferably B and $B^3$ are the same.

When X is a group of formula (IVF) preferably B is a group of formula $—[(CR^4_2CR^4_2)_bO]_cCR_2CR^4_2—$, eg. $—(CH_2CH_2O)_cCH_2CH_2—$.

Further groups bearing a centre of permanent positive charge are of formula (VA), (VB) and (VC). These groups also contain an alkyl or fluoroalkyl group capable of binding to a surface by physisorption. Monomers containing such a group are therefore particularly suitable for use in the polymers of the invention, optionally without separate comomoners containing a group capable of binding to a hydrophobic surface by physisorption.

The groups of formula (VA) are:

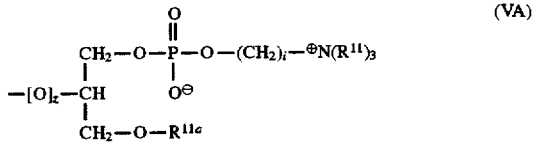

wherein the groups $R^{11}$ are the same or different and each is hydrogen or $C_{1-4}$ alkyl, $R^{11a}$ is either (a) a group —$[C(O)]_{vw}$ $(CR^{11b}_2)_{ww}$ $(SiR^{11c}_2)$ $(OSiR^{11c}_2)_{vv}$ $R^{11c}$ in which each group $R^{11b}$ is the same or different and is hydrogen or alkyl of 1 to 4 carbon atoms, each group $R^{11c}$ is the same or different and is alkyl of 1 to 4 carbon atoms or aralkyl, for example benzyl or phenethyl, vw is 0 or 1, ww is from 0 to 6 with the proviso that vw and ww are not both 0, and vv is from 0 to 49;

(b) a group of formula —$C(O)B^4$—$R^{11d}$, in which $R^{11d}$ is hydrogen or methyl, $B^4$ is a valence bond or straight or branched alkylene, oxaalkylene or oligo-oxaalkalyene group optionally containing one or more fluorine atoms, and containing from 6 to 24, preferably 6 to 18 carbon atoms; i is from 1 to 4; and if B is other than a valence bond Z is 1 and if B is a valence bond Z is 0 if X is directly bonded to an oxygen or nitrogen atom and otherwise Z is 1.

Preferably the groups $R^{11}$ are the same. It is also preferable that at least one of the groups $R^{11}$ is methyl, and more preferable that the groups $R^{11}$ are all methyl.

Preferably i is 1 or 2, more preferably 2.

Where $R^{11a}$ is a siloxane group as defined in (a) above, each group $(CR^{11b}_2)$ may be the same or different, preferably the same, and preferably each group $R^{11b}$ is hydrogen. Preferably ww is from 2 to 4, and is most preferably 3 when vw is 0 or 2 when vw is 1. Each group $(SiR^{11c}_2)$ may be the same or different, preferably the same, and preferably each group $R^{11c}$ is methyl. Preferably vv is from 4 to 29.

Preferably the group $R^{11a}$ is a group —$C(O)B^4R^{11d}$ as defined above. In such a case, preferably $B^4$ is:

a valence bond;

an alkylene group of formula —$(CR^{3d}_2)_{ad}$—, wherein the groups —$(CR^{3d}_2)$— are the same or different, and in each group —$(CR^{3d}_2)$— the groups $R^{3d}$ are the same or different and each group $R^{2d}$ is hydrogen, fluorine or $C_{1-4}$ alkyl or fluoroalkyl, preferably hydrogen or fluorine, and ad is from 1 to 24, preferably 6 to 18;

an oxaalkylene group such as alkoxyalkyl having 1 to 6 carbon atoms and optionally one or more fluorine atoms in each alkyl moiety, or an oligo-oxalkylene group of formula —$[(CR^{4d}_2)_{bd}O]_{cd}$— where the groups —$(CR^{4d}_2)$— are the same or different and in each group —$(CR^{4d}_2)$— the groups $R^{4d}$ are the same or different and each group $R^{4d}$ is hydrogen, fluorine or $C_{1-4}$ alkyl or fluoroalkyl, preferably hydrogen or fluorine, and bd is from 2 to 6, preferably 3 or 4, and cd is from 1 to 12, preferably 1 to 6.

When $B^4$ is a group —$[(CR^{4d}_2)_{bd}O]_{cd}$— wherein all the groups $R^{4d}$ are hydrogen and in all the groups —$[(CR^{4d}_2)_{bd}O]$— bd is 2, the residues of the monomer of formula (VA) are not able to form strong secondary valence interactions with hydrophobic surfaces. Whilst residues of such monomers may be included in the polymers of the invention, it is usually also necessary to include residues of monomers which are capable of forming strong secondary valence interactions if such interactions are to bind a polymer to a surface.

Monomers which have groups containing oligo(higher alkylene) oxide moieties can be used to provide strong secondary valence interactions, so can monomers which contain oligo alkylene oxide moieties in which at least 50, preferably 70, more preferably 90 mol % of individual alkylene oxide units contain 3 or more carbon atoms. Thus, for instance a mixed oligo(ethylene oxide/propylene oxide) side chain could be used provided that there are more propylene oxide units than ethylene oxide units.

When $B^4$ is a group —$[(CR^4_2)_{bd}O]$— then preferably bd is 2 in only 50, preferably 70, more preferably 90 mole % or less of the residues —$[(CR^{4d}_2)_{bd}O$—.

When the group —$B^4$—$R^{11a}$ is a group capable of forming strong secondary valence interactions with a surface, then monomers containing a group (VA) may be particularly suitable for use as monomers containing a group bearing a centre of permanent positive charge and an alkyl or fluoroalkyl group optionally containing one or more etheric oxygen atoms. Preferably, in such a case —$B^4$—$R^{11a}$ is an alkyl group optionally containing one or more etheric oxygen atoms and preferably 6 or more carbon atoms or a fluoroalkyl group optionally containing one or more etheric oxygen atoms and preferably 6 or more carbon atoms.

In one embodiment B and $B^4$ may be the same.

The groups of formula (VB) are:

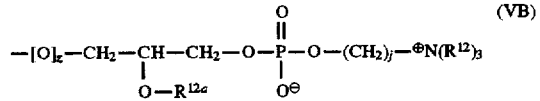

wherein the groups $R^{12}$ are the same or different and each is hydrogen or $C_1$-$C_4$ alkyl, $R^{12a}$ is either (a) a group —$[C(O)]_{tu}$ $(CR^{12b}_2)_{uu}$ $(SiR^{12c}_2)$ $(OSiR^{12c}_2)_{tt}$ $R^{12c}$ in which each group $R^{12b}$ is the same or different and is hydrogen or alkyl of 1 to 4 carbon atoms, each group $R^{12c}$ is the same or different and is alkyl of 1 to 4 carbon atoms or aralkyl, for example benzyl or phenethyl, tu is 0 or 1, uu is from 0 to 6, with the proviso that tu and uu are not both 0, and tt is from 0 to 49; or (b) a group of formula —$C(O)B^5$—$R^{12d}$ in which $R^{12d}$ is hydrogen or methyl, $B^5$ is a valence bond or a straight or branched alkylene, oxaalkylene or oligo-oxaalkylene group optionally containing one or more fluorine atoms and from 6 to 24 carbon atoms, more preferably 6 to 18 carbons atoms, j is from 1 to 4; and if B is other than a valence bond, Z is 1 and if B is a valence bond Z is 0 if X is directly bonded to an oxygen or nitrogen atom and otherwise Z is 1.

Preferably the groups $R^{12}$ are the same. It is also preferable that at least one of the groups $R^{12}$ is methyl, and more preferable that the groups $R^{12}$ are all methyl.

Preferably j is 1 or 2, more preferably 2.

Where $R^{12a}$ is a siloxane group as defined in (a) above, each group $(CR^{12b}_2)$ may be the same or different, preferably the same, and preferably each group $R^{12b}$ is hydrogen. Preferably uu is from 2 to 4, and is most preferably 3 when tu is 0 or 2 when tu is 1. Each group $(SiR^{12c}_2)$ may be the same or different, preferably the same, and preferably each group $R^{12c}$ is methyl. Preferably tt is from 4 to 29.

Preferably the group $R^{12c}$ is a group $—C(O)B^4R^{12d}$ as defined above. In such a case, preferably $B^5$ is:

a valence bond;

an alkylene group of formula $—(CR^{3c}_2)_{ac}—$, wherein the groups $—(CR^{3c}_2)—$ are the same or different, and in each group $—(CR^{3c}_2)—$ the groups $R^{3c}$ are the same of different and each group $R^{3c}$ is hydrogen, fluorine or $C_{1-4}$ alkyl, or fluoroalkyl, preferably hydrogen or fluorine, and ae is from 1 to 24, preferably 6 to 18;

an oxaalkylene group such as alkoxyalkyl having 1 to 6 carbon atoms and optionally one or more fluorine atoms in each alkyl moiety; or an oligo-oxaalkylene group of formula $—[(CR^{4c}_2)_{bc}—$ where the groups $—(CR^{4c}_2)—$ are the same or different and in each group $—(CR^{4c}_2)—$ the groups $R^{4c}$ are the same or different and each group $R^{4c}$ is hydrogen, fluorine or $C_{1-4}$ alkyl or fluoroalkyl, preferably hydrogen or fluorine, and be is from 2 to 6, preferably 3 or 4, and ce is from 1 to 12, preferably 1 to 6.

When $B^5$ is a group $—[(CR^{4c}_2)_{bc}O]—$ wherein all the groups $R^{4c}$ are hydrogen and in all the groups $[CR^{4c}_2)_{bc}O]$ be is 2, the residues of the monomer of formula (VB) are not able to form strong secondary valence interactions with hydrophobic surfaces. Whilst residues of such monomers may be included in the polymers of the invention, it is also necessary to include residues of monomers which are capable of forming such strong secondary valence interactions if such interactions are to bind a polymer to a surface. Monomers which have groups containing oligo(higher alkylene) oxide moieties can be used to provide the necessary strong secondary valence interactions, so can monomers which contain oligo alkylene oxide moieties in which at least 50, preferably 70, more preferably 90 mol % of individual alkylene oxide units contain 3 or more carbon atoms. Thus, for instance a mixed oligo(ethylene oxide/propylene oxide) side chain could be used provided that there are more propylene oxide units than ethylene oxide units.

When $B^5$ is a group $—[(CR^{4c}_2)_{bc}O]_{cc}—$ then preferably be is 2 in only 50, preferably 70, more preferably 90 mole % or less of the residues $—C(CR^{4b}_2)_{bc}O]—$.

When the group $—B^5—R^{12a}$ is a group capable of forming strong secondary valence interactions with a surface, then monomers containing a group (VB) may be particularly suitable for use as monomers containing a group bearing a centre of permanent positive charge and an alkyl or fluoroalkyl group optionally containing one or more etheric oxygen atoms. Preferably, in such a case $—B^5—R^{12\ a}$ is an alkyl group optionally containing one or more etheric oxygen atoms and preferably 6 or ore carbon atoms or a fluoroalkyl group optionally containing one or more etheric oxygen atoms and preferably 6 or more carbon atoms.

In one embodiment B and $B^5$ may be the same.

The groups of formula (VC) are:

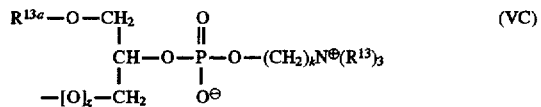

wherein the groups $R^{13}$ are the same or different and each is hydrogen or $C_{1-4}$ alkyl, $R^{13a}$ is either (a) a group $—[C(O)]_{rs}(CR^{13b}_2)_{ss}(SiR^{13c}_2)(OSiR^{13c}_2)_{rr}R^{13c}$ in which each group $R^{13b}$ is the same or different and is hydrogen or alkyl of 1 to 4 carbon atoms, each group $R^{13c}$ is the same or different and is alkyl of 1 to 4 carbon atoms or aralkyl, for example benzyl or phenethyl, rs is 0 or 1, ss is from 0 to 6, with the proviso that rs and ss are not both 0, and rr is from 0 to 49; or (b) a group of formula $—C(O)B^6—R^{13d}$, in which $R^{13a}$ is hydrogen or methyl, $B^6$ is a valence bond or a straight or branched alkylene, oxaalkylene or oligo-oxaalkylene group optionally containing one or more fluorine atoms and from 6 to 24, more preferably 6 to 18 carbon atoms and k is from 1 to 4; and if B is other than a valence bond, Z is 1 and if B is a valence bond Z is 0 if X is directly bonded to an oxygen or nitrogen atom and otherwise Z is 1.

Preferably the groups $R^{13}$ are the same. It is also preferable that at least one of the groups $R^{13}$ is methyl, and more preferable that the groups $R^{13}$ are all methyl.

Preferably k is 1 or 2, more preferably 2.

Where $R^{13a}$ is a siloxane group as defined in (a) above, each group $(CR^{13b}_2)$ may be the same or different, preferably the same and preferably each group $R^{13b}$ is hydrogen. Preferably ss is from 2 to 4, and is most preferably 3 when rs is 0 or 2 when rs is 1. Each group $(SiR^{13c}_2)$ may be the same, or different, preferably the same, and preferably each group $R^{13c}$ is methyl. Preferably rr is from 4 to 29.

Preferably the group $R^{13a}$ is a group $—C(O)B^6R^{13d}$ as defined above. In such a case, preferably $B^6$ is:

a valence bond;

an alkylene group of formula $—(CR^{3f}_2)_{af}—$, wherein the groups $—(CR^{3f}_2)—$ are the same or different, and in each group $— (CR^{3f}_2)—$ the groups $R^{3f}$ are the same or different and each group $R^{3f}$ is hydrogen, fluorine or $C_{1-4}$ alkyl or fluoroalkyl, preferably hydrogen or fluorine, and is from 1 to 24, preferably 6 to 18;

an oxaalkylene group such as alkoxyalkyl having 1 to 6 carbon atoms and optionally one or more fluorine atoms in each alkyl moiety; or an oligo-oxaalkylene group of formula $—[(CR^{4f}_2)_{bf}O]_{cf}—$ where the groups $—(CRf_2)—$ are the same or different and in each group $—(CR^{4f}_2)—$ the groups $R^{4f}$ are the same or different and each group $R^{4f}$ is hydrogen, fluorine or $C_{1-4}$ alkyl or fluoroalkyl, preferably hydrogen or fluorine, and bf is from 2 to 6, preferably 3 or 4, and cf is from 1 to 12, preferably 1 to 6.

When $B^6$ is a group $—[(CR^{4f}_2)_{bf}O]_{cf}—$ wherein all the groups $R^{4f}$ are hydrogen and in all the groups $[(CR^{4c}2)_{bf}O]$ bf is 2, the residues of the monomer of formula (VC) are not able to form strong secondary valence interactions with hydrophobic surfaces. Whilst residues of such monomers may be included in the polymers of the invention, it is also necessary to include residues of monomers which are capable of forming such strong secondary valence interactions if such interactions are to bind a polymer to a surface. Monomers which have groups containing oligo(higher alkylene) oxide moieties can be used to provide the necessary strong secondary valence interactions, so can monomers which contain oligo alkylene oxide moieties in which at least 50, preferably 70, more preferably 90 mol % of individual alkylene oxide units contain 3 or more carbon atoms. Thus, for instance a mixed oligo(ethylene oxide/propylene oxide) side chain could be used provided that these are more propylene oxide units then ethylene oxide units.

When $B^6$ is a group —$[(CR^{4f}_2)_{bf}O]_{cf}$— then preferably bf is 2 in only 50, preferably 70, more preferably 90 mol % or less of the residues —$[(CR^{4f}_2)_{bf}O]$—.

When the group —$B^6$—$R^{13a}$ is a group capable of forming strong secondary valence interactions with a surface, then monomers containing a group (VC) may be particularly suitable for use as monomers containing a group bearing a centre of permanent positive charge and an alkyl or fluoroalkyl group optionally containing one or more etheric oxygen atoms. Preferably, in such a case —$B^6$—$RI^{13a}$ is an alkyl group optionally containing one or more etheric oxygen atoms and preferably 6 or more carbon atoms or a fluoroalkyl group optionally containing one or more etheric oxygen atoms and preferably 6 or more carbon atoms.

In one embodiment B and $B^6$ may be the same.

Particular examples of preferred monomers bearing a group containing a centre of permanent positive charge are 2 (methacryloyloxy) ethyl-2'(trimethylammonium) ethyl phosphate inner salt and 1[(4(4'-vinylbenzyloxy)butane]-2" (trimethylammonium)ethyl phosphate inner salt.

Monomers bearing a group containing a centre of permanent positive charge, such as those of formula (II) and (III) may be prepared by conventional techniques using known reactions, for example using a suitable substituted alkyl (alk)acrylate or suitable substituted styrene as precursor. Examples of suitable substituted alkyl (alk)acrylates include dimethylaminoethyl(meth)acrylate and 2-hydroxyethyl (meth) acrylate.

Monomers of formula (II) or (III) containing a group of formula (IVA) may be prepared by known methods. Monomers containing a group of formula (IVB) or (IVC) may be prepared as described in Reference Example 1 to 3 or by analogous known methods.

Monomers of formula (II) or (III) containing a group of formula (IVD) in which $R^{3a}$ is —$C(O)B^1R^{3b}$ may be prepared by selective acylation of glycerophosphorylcholine or analogues thereof at the primary hydroxyl group with an activated acid derivative such as an acid anhydride $O(C(O)B^1R^{3b})_2$ or an acid halide $R^{8b}B^1BCOHal$ where $B^1$ and $R^{8b}$ are as defined above and Hal is halogen, followed by acylation of the secondary hydroxyl group with an appropriate acylating agent, for example methacryloyl chloride. Purification, for example by column chromatography on a suitable support, may be performed after each acylation or after the second acylation only. Suitable activated acid derivatives include acid anhydrides, acid halides, reactive esters and imidazolides. The acylations may be performed in a suitable anhydrous, aprotic solvent, for example N,N-dimethylformamide, optionally in the presence of a suitable non-nucleophilic base, for example triethylamine.

Alternatively, the primary alcohol group in glycerophosphoryl choline or an analogue thereof may be blocked by reaction with a suitable protecting group reagent, for example t-butyldimethylsilyl chloride, under standard conditions and the secondary hydroxy group then treated with an acylating agent such as methacryloyl chloride. The t-butyldimethylsilyl protecting group may be removed by treatment with a dilute organic or mineral acid, for example p-toluene sulphonic acid, hydrochloric acid or with tetrabutylammonium fluoride. The deblocked primary hydroxyl group may then be treated with an activated acid derivative such as an acid anhydride $O(C(O)B^1R^{8b})_2$ or acid halide $R^{8b}B^1COHal$ where $B^1$ and $R^{8b}$ are as defined above, and Hal is halogen.

Analogues of glycerophosphorylcholine (compounds of formual (II) or (III) containing a group (IVD) where $R^{8a}$ is hydrogen) may be prepared by reaction of phosphorus oxychloride with a bromoalcohol in an inert aprotic solvent, such as dichloromethane, to give a bromoalkylphosphorodichloridate. The dichloro derivative thus produced may then be treated with an appropriately protected glycerol derivative, for example 2,2-dimethyl 1,3-dioxolane-4-methanol, in the presence of a base, for example triethylamine, followed by acid hydrolysis to give a bromoalkylphosphoro-glycerol derivative. This may then be treated with an amine $NR^8_{31}$ where $R^8$ is as defined above, for example trimethylamine, to generate the glycerophosphorylcholine analogue. This preparation is depicted in the following scheme.

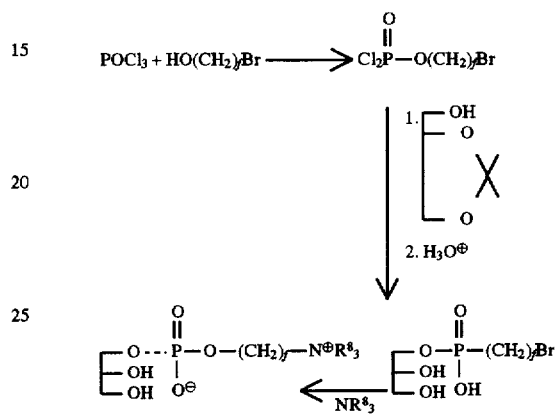

where $R^8$ and f are as defined in relation to groups of formula (IVD).

Monomers of formula (II) or (III) containing a group of formula (IVE) in which $R^{9a}$ is —$C(O)B^2R^{9b}$ may be prepared by the selective acylation of glycerophosphorylcholine or an analogue thereof at the primary hydroxyl group with for example, methacryloyl chloride followed by reaction at the secondary hydroxyl group using an activated acid derivative, such as an acid halide $O(C(O)B^2R^{9b})_2$ or an acid halide $R^{9b}B^2COHal$, where $B^2$ and $R^{9b}$ are as defined above and Hal is halogen. The intermediates and final products may be purified, as necessary using column chromatography. Optionally, protecting group strategy, similar to that outlined above in relation to production of monomers containing a group of formula (IVD) may be employed.

Monomers of formula (II) or (III) containing a group of formula (IVF) may be prepared in an analogous manner to monomers containing groups of formula (IVD) or (IVE).

Monomers of formula (II) or (III) containing a group of formula (VA), (VB) or (VC) may be prepared by direct analogy with methods described for monomers containing groups of formula (IVD), (IVE) and (IVF) respectively.

Comonomers Capable of Stably Binding a Polymer to a Surface

In the polymer of the invention, where the group bearing a centre of permanent positive charge and group capable of stably binding the polymer to a surface are not present in the residue of the same monomer, the polymer comprises residues of comonomer containing a group capable of stably binding a polymer to a surface as well as the residues of the comonomer containing a group bearing a centre of permanent positive charge. Optionally, where the monomer containing a group bearing a centre of permanent positive charge also contains a group capable of stably binding the polymer to a surface, further groups capable of stably binding to a surface may be provided by additional comonomer residues containing a group capable of binding the polymer to a surface.

As has already been mentioned, the nature of the group capable of binding to a surface, and therefore the nature of the comonomers containing such groups, will depend upon the nature of the surface which is to be coated with the polymer. The various types of such comonomers will now be described.

It will be appreciated that in some circumstances it may be desirable to use a combination of different comonomers containing groups capable of binding to a surface. Preferably a comonomer of type a), b) and/or c) as defined below or a combination of such comonomers is used, more preferably only one of comonomer types a), b) and c) is used.

a) Comonomers containing an alkyl, fluoroalkyl or siloxane group

The comonomers containing an alkyl, fluoroalkyl or siloxane group, which are suitable for providing binding to a hydrophobic surface, are comonomers containing an alkyl group of 6 or more carbon atoms which group optionally contains one or more etheric oxygen atoms and optionally one or more carbon-carbon double or triple bonds or a fluoroalkyl group, preferably of 6 or more carbon atoms, which group optionally contains one or more etheric oxygen atoms and optionally one or more carbon-carbon double or triple bonds, or containing a siloxane group, containing up to 50 silicon atoms, preferably in a linear chain.

Preferably the alkyl or fluoroalkyl groups contains up to 24 carbon atoms, for instance up to 18 carbon atoms, or containing a siloxane group, containing up to 50 silicon, preferably in a linear chain. Preferred comonomers containing an alkyl, fluoroalkyl or siloxane group are those of general formula (VI)

$$Y^1—Q \quad (VI)$$

where $Y^1$ is an ethylenically unsaturated polymerisable group selected from

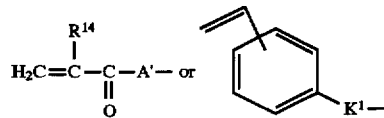

where $R^{14}$ is hydrogen or $C_1-C_4$ alkyl,

A' is —O— or —NR$^{15}$— where $R^{15}$ is hydrogen or a $C_1-C_4$ alkyl group or $R^{15}$ is a group Q;

$K^1$ is a group —(CH$_2$)$_l$OC(O)—, —(CH)$_l$C(O)O—, —(CH$_2$)$_l$OC(O)O—, —(CH$_2$)$_l$NR$^{16}$—, —(CH$_2$)$_l$NR$^{16}$C(O)—, —(CH$_2$)$_l$C(O) NR$^{16}$—, —(CH$_2$)$_l$NR$^{16}$C(O)O—, —(CH$_2$)$_l$OC(O)NR$^{16}$—, —(CH$_2$)$_l$INR$^{16}$C(O) NR$^{16}$— (in which the groups $R^{16}$ are the same or different), —(CH$_2$)$_l$O—, —(CH$_2$)$_l$SO$_3$—, a valence bond and l is from 1 to 12 and $R^{16}$ is hydrogen or a $C_1-C_4$ alkyl group; and Q is (a) a straight or branched alkyl, alkoxyalkyl or (oligo-alkoxy)alkyl chain containing 6 or more, preferably 6 to 24, carbon atoms unsubstituted or substituted by one or more fluorine atoms and optionally containing one or more carbon-carbon double or triple bonds; or (b) a siloxane group —(CR$^{16a}$$_2$)$_{qq}$(SiR$^{16b}$$_2$)(OSiR$^{16b}$$_2$)$_{pp}$R$^{16b}$ in which each group R$^{16a}$ is the same or different and is hydrogen or alkyl of 1 to 4 carbon atoms or aralkyl, for example benzyl or phenethyl, each group R$^{16b}$ is alkyl of 1 to 4 carbon atoms, qq is from 1 to 6 and pp is from 0 to 49.

Preferred comonomers of formula (VI) bearing a group Q include those of formula (VII) and (VIII):

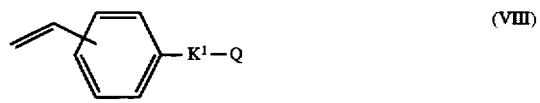

wherein:

$R^{14}$, A', $K^1$ and Q are as defined in relation to formula (VI).

Preferably in the compounds of formula (VII) $R^{14}$ is hydrogen methyl or ethyl, more preferably methyl so that the compound of formula (VII) is preferably an acrylic acid, methacrylic acid or ethacrylic acid derivative.

In the compounds of formula (VIII) $K^1$ may for instance be a valence bond. Where $K^1$ is a group then preferably l is from 1 to 6, more preferably 1, 2 or 3 and most preferably l is 1. When $K^1$ is a group —(CH$_2$)$_l$NR$^{16}$—, —(CH$_2$)$_l$OC (O)NR$^{16}$—, —(CH$_2$)$_l$NR$^{16}$C(O)O—, —(CH$_2$)$_l$NR$^{16}$C(O)—, —(CH$_2$)$_l$C(O)NR$^{16}$— or —(CH$_2$)$_l$NR$^{16}$C(O)NR$^{16}$— then $R^{16}$ is preferably hydrogen, methyl or ethyl, more preferably hydrogen.

In the compounds of formula (VIII), preferably the vinyl group is para to the group —$K^1$—Q.

Preferably Q is an alkyl or fluoroalkyl group optionally containing one or more etheric oxygen atoms and optionally one or more carbon-carbon double or triple bonds. More preferably Q is:

an alkyl group of formula —(CR$^{17}$$_2$)$_m$CR$^{17}$$_3$, wherein the groups —(CR$^{17}$$_2$)— are the same or different, and in each group —(CR$^{17}$$_2$)— the groups R$^{17}$ are the same or different and each group R$^{17}$ is hydrogen, fluorine or $C_{1-4}$ alkyl or fluoroalkyl and m is from 5 to 23 if Q contains no fluorine atoms or from 1 to 23, preferably 5 to 23, if Q contains one or more fluorine atoms;

an alkoxyalkyl having 1 to 12 carbon atoms in each alkyl moiety; unsubstituted or substituted by one or more fluorine atoms; or an (oligo-alkoxyl) alkyl group of formula —[(CR$^{18}$$_2$)$_s$O]$_o$(CR$^{18}$$_2$)$_s$R$^{18}$ where the groups —(CR$^{18}$$_2$)— are the same or different and in each group —(CR$^{18}$$_2$)— the groups R$^{18}$ are the same or different and each group R$^{18}$ is hydrogen, fluorine or $C_{1-4}$ alkyl or fluoroalkyl and n is from 2 to 6, preferably 3 to 4, and o is from 1 to 12.

When Q is a group —[(CR$^{18}$$_2$)$_s$O]$_o$(CR$^{18}$$_2$)$_s$R$^{18}$ wherein all the groups R$^{18}$ are hydrogen and in all the groups —[(CR$^{18}$$_2$)$_s$O]— n is 2 the group of formula Q is not able to form strong secondary valence interactions with hydrophobic surfaces. Whilst residues of monomers containing such a group may be included in the polymers of the invention, it is also necessary to include residues of monomers which are capable of forming such strong secondary valence interactions if such interactions are to bind a polymer to a surface. Monomers which have groups containing oligo(higher alkylene) oxide moieties can be used to provide monomers which contain oligo alkylene oxide moieties in which at least 50mol % of individual alkylene oxide units contain 3 or more carbons atoms. Thus, for instance a mixed oligo(ethylene oxide/propylene oxide) side chain could be used provided that there are more propylene oxide units than ethylene oxide units.

Where Q is an (oligo-alkoxy)-alkyl group containing residues —[(CR$^{18}_2$)$_s$O]— wherein n is 2, then preferably n is 2 in no more than 50 mol % of the residues —[(CR$^{18}_2$)$_s$O]—.

Alternatively, Q may be a group in which one or more of the alkyl or alkylene moieties in such an alkyl, alkoxyalkyl or (oligoalkoxy) alkyl group is replaced by a corresponding alkenyl, alkynyl, alkenylene or alkynylene moiety.

Preferred groups Q include alkyl, alkoxyalkyl and (oligo-alkoxy)alkyl groups optionally containing one or more carbon-carbon double or triple bonds of 8 or more, more preferably 10 or more, even more preferably 12 or more, for instance 14 or more, such as 16 or more carbon atoms. Such groups may contain one or more fluorine atoms and be therefore fluoroalkyl derivatives. Preferably however, such groups do not contain any fluorine atoms.

Particularly preferred groups are straight chain alkyl or fluoroalkyl groups optionally containing one or more carbon-carbon double or triple bonds.

Where Q is a siloxane group, each group —(CR$^{16a}_2$)— may be the same or different, preferably the same, and preferably each group R$^{16a}$ is hydrogen. Preferably qq is from 2 to 4, and is most preferably 3. Each group —(SiR$^{16b}_2$)— may be the same or different, preferably the same, and preferably each group R$^{16b}$ is methyl. Preferably pp is from 4 to 29. Preferred comonomers where Q is a siloxane group are those of formula (VII).

In one specific embodiment the group Q does not contain any ethylenic unsaturation, i.e. any carbon-carbon double or triple bonds.

Particular examples of comonomers containing an alkyl, fluoroalkyl or siloxane group include: n-dodecyl methacrylate, octadecyl methacrylate, hexadecyl methacrylate, 1H,1H,2H,2H-heptadecafluorodecyl methacrylate, p-octyl styrene, p-dodecyl styrene and monomethacryloxypropyl terminated siloxanes. n-Dodecyl methacrylate is particularly preferred.

Comonomers containing a physisorbable alkyl or fluoroalkyl, which does not contain a carbon-carbon double or triple bond, or a siloxane group such as those of formulae (VII) and (VIII) are commercially available or may be prepared by conventional techniques using known reactions.

In a second specific embodiment of such comonomers, the group Q does contain ethylene unsaturation, i.e. one or more carbon-carbon double or triple bonds. Such comonomers may for example contain a vinylic, divinylic, acetylenic or diacetylenic moiety. Comonomers containing acetylenic rather than vinylic unsaturation are in general preferred, especially those containing a single acetylenic group.

Comonomers which contain such an ethylenic unsaturated group are capable of providing crosslinking between linear polymer claims once the polymer is coated onto a substrate, as well as binding to the substrate by physisorption. Such crosslinking may improve the stability of the coating and is typically formed by irradiation, for example with UV-or gamma-radiation. The crosslinking of such groups may be employed either alone or in addition to the use of a comonomer containing a reactive group as a crosslinkable comonomer as described below.

Particularly preferred crosslinkable comoners capable of binding to a substrate by physisorption are those of formula (VIIA) and (VIIIA)

$CH_2=CR^{14}-C(O)-A'-QQ$       (VIIA)

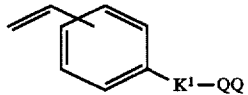  (VIIIA)

in which R$^{14}$, A' and K$^1$ are as hereinbefore defined and QQ is an alkynyl group containing 6 or more carbon atoms and one or two, preferably one, carbon-carbon triple bonds provided that the acetylenic moieties are not directly bonded to A' or K$^1$.

The present invention provides, as a further feature, comonomers of formula (VIIA) and (VIIIA).

Amongst such comonomers it is preferred that QQ is a group containing from 6 to 24 carbon atoms, preferably 8 or more, more preferably 10 or more, even more preferably 12 or more, for instance 14 or more, such as 16 or more carbon atoms.

It is also preferred that the group QQ does not contain a terminal acetylenic moiety, i.e. a group —C≡CH.

A particularly preferred group QQ is 7-dodecynyl and a specific example of a compound of formula (VIIA) containing such a group is dodec-7-yn-1-ol methacrylate.

The compound of formula (VIIA) and (VIIIA) and other comonomers of formula (VII) and (VIII) containing an ethylenically unsaturated physisorable group Q, may be prepared by anology with known methods. Their preparation is illustrated by Reference Example 5.

b) Comonomers bearing a reactive group

Preferred comonomers, which are suitable for providing binding to a hydrophilic surface having functional groups, contain a reactive group capable of covalently binding to a surface and are of general formula (IX)

$Y^2-Q^1$       (IX)

where Y$^2$ is an ethylenically unsaturated polymerisable group selected from

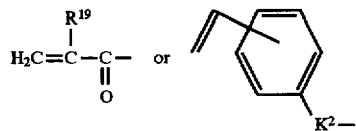

where R$^{19}$ is hydrogen or C$_1$-C$_4$ alkyl,

K$^2$ is a group —(CH$_2$)$_q$OC(O)—, —(CH)$_q$C(O)O—, —(CH$_2$)$_q$OC(O)O—, 13 (CH$_2$)$_q$NR$^{20}$—, —(CH$_2$)$_q$NR$^{20}$C(O) —, —(CH$_2$)$_q$C(O)NR$^{20}$—, —(CH$_2$)$_q$NR$^{20}$C(O)O—, —(CH$_2$)$_q$OC(O)NR$^{20}$—, —(CH$_2$)$_q$NR$^{20}$C(O)NR— (in which the groups R$^{20}$ are the same or different), —(CH$_2$)$_q$O—, or —(CH$_2$)$_q$SO$_3$—, or a valence bond and q is from 1 to 12 and R$^{20}$ is hydrogen or a C$_1$-$_4$ alkyl group; and Q$^1$ is a reactive group capable of reacting to provide covalent binding to a surface.

Preferred comonomers of formula (IX) bearing a reactive group Q$^1$ include those of formula (X) and (XI) defined below.

The compounds of formula (X) are:

$$\begin{array}{c} R^{19} \\ | \\ CH_2{=}C \\ | \\ C{-}Q^2 \\ \| \\ O \end{array} \quad (X)$$

wherein:

$R^{19}$ is as defined with reference to formula (X), and $Q^2$ is a reactive group.

Preferably in the compounds of formula (X) $R^{19}$ is hydrogen, methyl or ethyl, more preferably methyl, so that the compound of formula (X) is preferably an acrylic acid, methacrylic acid or ethacrylic acid derivative.

Preferably $Q^2$ is hydrogen, or more preferably —OH or a group of the formula:

$$—T—B^7—Q^3$$

where

T is —O—, or —NR$^{21}$ where R$^{21}$ is hydrogen, $C_1$-$C_4$ alkyl or a group —B$^7$—Q$^3$;

B$^7$ is a valence bond or, more preferably, a straight or branched alkylene, oxaalkylene or oligo-oxaalkylene chain; and Q$^3$ is a reactive group capable of reacting to provide covalent binding to a surface such as an aldehyde group or a silane or siloxane group containing one or more reactive substituents such as halogen, for example chlorine, or alkoxy, generally containing from 1 to 4 carbon atoms, for example methoxy or ethoxy, or, more preferably Q$^3$ is a hydroxyl, amino, carboxyl, epoxy, —CHOHCH$_2$Hal, (in which Hal is a halogen atom such as chlorine, bromine or iodine) succinimido, tosylate such as 2(N-methylpyridinium) tosylate, triflate, imidazole carbonyl-amino, or an optionally substituted triazine group.

Preferably B$^7$ is:

an alkylene group of formula —(CR$^{22}$$_2$)$_r$—, wherein the groups —(CR$^{22}$$_2$)— are the same or different, and in each group —(CR$^{22}$)— the groups R$^{22}$ are the same or different and each group R$^{22}$ is hydrogen or $C_{1-4}$ alkyl, preferably hydrogen, and r is from 1 to 12, preferably 1 to 6;

an oxaalkylene group such as alkoxyalkyl having 1 to 6 carbon atoms in each alkyl moiety; or an oligo-oxaalkylene group of formula —[(CR$^{23}$$_2$)$_s$O]$_t$ (CR$^{23}$$_2$)$_s$— where the groups —(CR$^{23}$$_2$)— are the same or different and in each group —(CR$^{232}$)— the groups R$^{23}$ are the same or different and each group R$^{23}$ is hydrogen or $C_{1-4}$ alkyl, preferably hydrogen, and s is from 1 to 6, preferably 2 or 3, and t is from 1 to 11, preferably 1 to 5.

Preferred groups B$^7$ include alkylene, oxaalkylene and oligo-oxaalkylene groups of up to 12 carbon atoms.

Where Q$^3$ is a silane or siloxy group, preferably B$^7$ is an alkylene group of 1 to 6, preferably 2 to 4, more preferably 3 carbon atoms.

Particular examples of the group B$^7$ are —CH$_2$—, —CH$_2$CH$_2$— and —(CH$_2$)$_6$—.

The compounds of formula (XI) are:

wherein K$^2$ is as defined in relation to formula (IX) and;

B$^8$ is a straight of branched alkylene, oxaalkylene or oligo-oxaalkylene chain and Q$^4$ is a reactive group capable of reacting to provide covalent binding to a surface, for example an aldehyde group or a silane or siloxane group containing one or more reactive substituents such as halogen, for example chlorine, or alkoxy, generally containing from 1 to 4 carbon atoms, for example methoxy or ethoxy, or, more preferably, Q$^4$ is a hydroxyl, amino, carboxyl, epoxy, —CHOHCH$_2$Hal, (in which Hal is a halogen atom such as chlorine, bromine or iodine) succinimido, tosylate, triflate, imidazole carbonyl-amino or optionally substituted triazine group.

In the compounds of formula (XI) preferably the vinyl group is para to the group —K$^2$—B$^8$—Q$^4$.

K$^2$ may for instance be a valence bond. Where K$^2$ is a group then preferably q is from 1 to 6, more preferably 1,2 or 3 and most preferably q is 1. When K$^2$ is a group —(CH$_2$)$_q$NR$^{20}$—, —(CH$_2$)$_q$OC(O)NR$^{20}$—, —(CH$_2$)$_q$NR$^{20}$C(O)O—, —(CH$_2$)$_q$NR$^{20}$C(O)—, —(CH$_2$)$_q$C(O) NR$^{20}$— or (CH$_2$)$_q$NR$^{20}$C(O)NR$^{20}$ — then R$^{20}$ is preferably hydrogen, methyl or ethyl, more preferably hydrogen.

Preferably B$^8$ is;

an alkylene group of formula —(CR$^{24}$$_2$)$_u$—, wherein the groups; —(CR$^{24}$$_2$)— are the same or different, and in each group —(CR$^{24}$$_2$)— the groups R$^{24}$ are the same of different and each group R$^{24}$ is hydrogen or $C_{1-4}$ alkyl, preferably hydrogen, and u is from 1 to 12, preferably 1 to 6;

an oxaalkylene group such as alkoxyalkyl having 1 to 6 carbon atoms in each alkyl moiety; or an oligo-oxaalkylene group of formula —[(CR$^{25}$$_2$)$_v$O]$_w$ (CR$^{25}$)$_v$— where the groups —(CR$^{25}$$_2$)— are the same or different and in each group —(CR$^{25}$$_2$)— the groups R$^{25}$ are the same or different and each group R$^{25}$ is hydrogen or $C_{1-4}$ alkyl, preferably hydrogen, and v is from 1 to 6, preferably 2 or 3, and w is from 1 to 12, preferably 1 to 6.

Preferred groups B$^8$ include alkylene, oxaalkylene and oligo-oxaalkylene groups of up to 12 carbon atoms. In one embodiment B$^8$ and K$^2$ contain together up to 12 carbon atoms.

Particular examples of comonomers bearing a reactive group include chloromethylstyrene, methacrylic acid, 2-aminoethylmethacrylate, 2,3-epoxypropyl methacrylate, 3-chloro-2-hydroxypropylmethacrylate, 2-methacryloyloxy- ethyl dichlorotriazine, 3-chloro-2-hydroxy-propylmethacrylamide and glycidyl methacrylate and reactive methacrylate esters containing the group HetC (O)O— in which (Het) is a heterocyclic ring, for example benzotriazole or imidazole and reactive methacrylate esters containing a group R$^{16}$OC(O)— in which R$^{16}$ is a succinimido or pentafluorophenyl group.

Particularly preferred comonomers bearing reactive groups are 2-aminoethyl-methacrylate and 3-chloro-2-hydroxypropylmethacrylate.

Comonomers bearing a reactive group capable of binding covalently to a surface, such as those of formula (X) or (XI), are commercially available or may be prepared by conventional techniques using known reactions.

Comonomers of formula (X), which are dichlorotriazine monomers may be prepared in known manner for example by reacting a substituted hydroxy-alkyl(alk)acrylate or aminoalkyl(alk)acrylate with trichlorotriazine in a suitable solvent and in the presence of a base.

Comonomers of formula (XI) which are reactive methacrylate esters in which the ester groups contains an imidazole group may be prepared in known manner by reacting a substituted hydroxyalkyl(alk)acrylate (e.g. 2-hydroxyethyl-(meth)acrylate), polyethylene-oxide(meth)acrylate or polypropyleneoxide (meth)acrylate with 1,1-carbonyldiimidazole in a dry solvent. Analogous known methods may be used to prepare succinimido and pentafluorophenyl methacrylate esters of formula (X), by reaction with a reactive ester, acid halide or acid anhydride.

Where comonomers containing a reactive group are used to bind a copolymer to a surface by covalent bonding, it will be appreciated that not all of the reactive groups need necessarily bind to surface reactive groups and that groups not so bound may participate in other chemistry. Such groups may in particular provide points for the attachment of moieties such as ligands to the polymer, when coated onto a substrate.

Comonomers containing a reactive group, such as compounds of formula (X) and (XI) may be used as comonomers containing crosslinkable groups, which react with other crosslinkable groups, rather than a monomer which bind covalently to a surface.

Where comonomers containing a reactive group are used to provide such crosslinkable groups then the crosslinkable groups and/or the copolymerisation conditions will be chosen so that they will not crosslink when the comonomers are copolymerised; thus the polymerisation product will be an uncrosslinked linear copolymer which may be subsequently crosslinked after coating the copolymer onto a surface so as to improve the stability of the coating. When such crosslinking between linear polymer chains is employed the crosslinkage may be formed either between two such crosslinkable groups or between a crosslinkable group and a non-inert group in a diluent comonomer residue (defined later). Such a crosslinkage may be formed either by direct reaction of the groups forming the crosslinkage or by reaction of these groups with a reactive bridging molelcule for example a reactive gas, such as ammonia.

Residues of such comonomers may therefore be present in polymers which are designed to coat hydrophobic surfaces and containing residues of a monomer containing a group bearing a centre of permanent positive charge which is of formula (VA), (VB) or (VC) or a comonomer containing an alkyl, fluoroalkyl or siloxane group, which is of formula (VII) or (VIII). Similarly residues of such comonomers may also be present in polymers designed to bind to a surface by ionic interaction and which contains residues of a compound of formula (XIII) or (XIV) as defined below.

Preferred reactive comonomers which are used to crosslink the comonomer, rather than provide covalent binding to the surface, are those of formula (X) or (XI) in which $Q^2$, or $Q^4$ contains a crosslinkable cinnamyl, epoxy, —CHOHCH$_2$Hal (in which Hal is a halogen atom), methylol, silyl, an ethylenically unsaturated crosslinkable group, such as an acetylenic, diacetylenic, vinylic or divinylic group, or an acetoacetoxy or chloroalkyl sulfone, preferably chloroethyl sulphone, group.

Particular examples of comonomers bearing a group capable of crosslinking include methacrolein, cinnamyl methacrylate, 2,3-epoxypropyl methacrylate, 3-chloro-2-hydroxypropyl methacrylate, hydroxymethyl methacrylamide, 3-(trimethoxysilyl)propyl methacrylate, 2-acetoacetoxyethyl methacrylate, 3-(vinylbenzyl)-2-chloroethyl sulfone.

When a polymer of the invention, containing crosslinkable groups, is coated on a substrate the polymer is in substantially uncrosslinked form. After coating, crosslinking of crosslinkable groups may be performed to increase the strength and stability of the polymer coating.

c) Comonomers bearing an ionic group

Preferred comonomers bearing an ionic group capable of binding to a surface by ionic interaction are of general formula (XII)

     (XII)

where $Y^2$ is an ethylenically unsaturated polymerisable group selected from

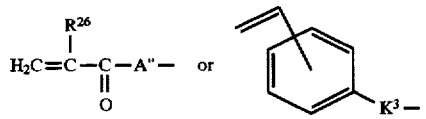

where $R^{26}$ is hydrogen or $C_1$–$C_4$ alkyl;

A" is —O— or —NR$^{27}$—, wherein $R^{27}$ is hydrogen or a $C_1$–$C_4$ alkyl group or $R^{27}$ is a group —B$^9$—Q$^5$;

$B^9$ is a valence bond, a straight or branched alkylene, oxaalkylene or oligo-oxaalkylene group;

$K^3$ is a group —(CH$_2$)$_x$OC(O)—, —(CH)$_x$C(O)O—, —(CH$_2$)$_x$OC(O)O—, —(CH$_2$)$_x$NR$^{28}$—, —(CH$_2$)$_x$NR$^{28}$C(O)—, —(CH$_2$)$_x$C(O)NR$^{28}$—, —(CH$_2$)$_x$NR$^{28}$C(O)O—, —(CH$_2$)$_x$OC(O)NR$^{28}$—, —(CH$_2$)$_x$NR$^{28}$C(O)NR$^{28}$— (in which the groups $R^{28}$ are the same or different), —(CH$_2$)$_x$O—, —(CH$_2$)$_x$SO$_3$—, a valence bond (optionally in combination with B9) and x is from 1 to 12 and $R^{28}$ is hydrogen or a $C_1$–$C_4$ alkyl group;

$Q^5$ is an ionic group capable of binding to a surface by ionic interaction.

Preferred comonomers of formula (XII) are therefore those of formula (XIII) and (XIV):

     (XIII)

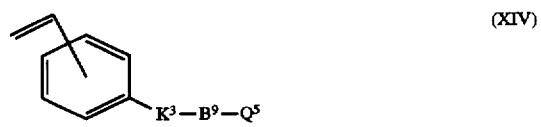     (XIV)

wherein:

$R^{26}$, A", $B^9$, $K^3$ and $Q^5$ are as defined in relation to formula (XII).

Preferably in the compounds of formula (XIII) $R^{26}$ is hydrogen, methyl or ethyl, more preferably methyl, so that the compound of formula (XIII) is preferably an acrylic acid, methacrylic acid or ethacrylic acid derivative.

In the compounds of formula (XIV), $K^3$ may for instance be a valence bond. Where $K^3$ is a group then x is preferably from 1 to 6, more preferably 1, 2 or 3 and most preferably x is 1. When $K^3$ is a group —(CH$_2$)$_x$NR$^{26}$—, —(CH$_2$)$_x$OC(O)NR$^{26}$—, —(CH$_2$)$_x$NR$^{26}$C(O)O—, —(CH$_2$)$_x$NR$^{26}$C(O)—, —(CH$_2$)$_x$C(O)NR$^{26}$— or —(CH$_2$)$_x$NR$^{26}$C(O)NR$^{26}$— then $R^{26}$ is preferably hydrogen, methyl or ethyl, more preferably hydrogen.

In the compounds of formula (XIV) preferably the vinyl group is para to the group $—K^3—B^8—Q^4$.

Preferably $B^9$ is:

an alkylene group of formula $—(CR^{29}_2)_y—$, wherein the groups $—(CR^{29}_2)—$ are the same or different, and in each group $—(CR^{29}_2)—$ the groups $R^{29}$ are the same or different and each group $R^{29}$ is hydrogen or $C_{1-4}$ alkyl, preferably hydrogen, and y is from 1 to 12, preferably 1 to 6;

an oxaalkylene group such as alkoxyalkyl having 1 to 6 carbon atoms in each alkyl moiety; or an oligo-oxaalkylene group of formula $—[(CR^{30}_2)_{yy}O]_{xx}(CR^{30}_2)_{yy}—$ where the groups $—(CR^{30}_2)—$ are the same or different and in each group $—(CR^{30}_2)—$ the groups $R^{30}$ are the same or different and each group $R^{30}$ is hydrogen or $C_{1-4}$ alkyl, preferably hydrogen, and yy is from 1 to 6, preferably 2 or 3, and xx is from 1 to 12, preferably 1 to 6.

Preferred groups $B^9$ include alkylene, oxaalkylene and oligo-oxaalkylene groups of up to 12 carbon atoms.

Particular examples of the group $B^9$ are $—CH_2—$, $—CH_2CH_2—$ and $—(CH_2)_6—$.

The group $Q^5$ may be either anionic or cationic depending pon the surface to be coated. Where the surface has a cationic surface charge, the group $Q^5$ will be anionic and may for example be a carboxylate, sulphonate, hydrogenphosphate or phosphate group. Where the surface has an anionic surface charge, the group $Q^5$ will be cationic and may for example by a group $—NR^{31}_3{}^\oplus$ in which each group $R^{31}$ is the same or different, and is hydrogen or alkyl of 1 to 6 carbon atoms two of which groups $R^{31}$ may together from a heterocyclic ring containing from 5 to 7 atoms, preferably hydrogen or methyl, a group $N^\oplus$ Het, where Het is an unsaturated heterocyclic group such as pyridyl, substituted or unsubstituted by one or more alkyl groups of 1 to 4 carbon atoms, or a group $—PR^{32}_3{}^\oplus$ in which each group $R^{32}$ is the same or differnt and is hydrogen or alkyl of 1 to 6 carbons atoms, two of which groups $R^{31}$ may together form a heterocyclic ring containing from 5 to 7 atoms, preferably methyl.

Particular examples of comonomers bearing an ionic group include acrylic acid, methacrylic acid, 2-sulfoethyl methacrylate, 2-methacryloyloxyethyl phosphate, p-styrene sulfonic acid, 2-(methacryloyloxyethyl) trimethylammonium chloride, 3-aminopropyl methacrylamide, vinylbenzyl trimethylammonium chloride.

Comonomers bearing a group capable of binding a polymer to a surface by ionic interaction, such as those of formula (XIII) and (XIV) are commercially available or may be prepared by conventional techniques using known reactions.

Diluent Comonomers

In addition to a) the residues of monomers containing a group bearing a centre of permanent positive charge or b) the residues of comonomers containing a group bearing a centre of permanent positive charge and comonomers which are capable of binding to a surface, the polymers of the present invention may comprise residues of a diluent comonomer.

Such diluent comonomers may be used to give the polymer the desired physical and mechanical properties. They may be of any known conventional radical polymerisable, preferably ethylenically unsaturated, type compatible with other comonomer(s).

Particular examples of diluent comonomers include alkyl (alk)acrylate preferably containing 1 to 4 carbon atoms in the alkyl group of the ester moiety, such as methyl (alk) acrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl (alk)acrylate; an alkyl (alk) acrylamide preferably containing 1 to 4 carbon atoms in the alkyl group of the amide moiety; a hydroxyalkyl (alk) acrylate preferably containing from 1 to 4 carbon atoms in the hydroxyalkyl moiety, e.g. a 2-hydroxyethyl (alk) acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Particularly suitable diluent comonomers include methacryloyl glucose or sorbitol methacrylate.

Further diluents which may be mentioned specifically include polymerisable alkenes, preferably of 2–4 carbon atoms, eg. ethylene, dienes such as butadiene, alkylene anhydrides such as maleic anhydride and cyano-substituted alkylenes, such as acrylonitrile.

Diluent comonomers may be obtained by conventional known methods.

Of the above diluent comonomers some are inert and act simply to modify the physical and mechanical properties of copolymers containing them. Others, and in particular the hydroxyalkyl(alk)acrylates and polyhydroxyl (alk)acrylates have a reactive role in addition to simply modifying physical and mechanical properties. Such comonomers contain functional groups, such as hydroxyl groups, which may react with a crosslinking group or may react with reactive groups in other molecules to attach them to the copolymer.

It will also be appreciated that alkyl(alk)acrylates containing 6 or more carbon atoms in the alkyl group may be regarded as either diluent comonomers or comonomers capable of binding a polymer to a surface by physisorption. In particular it should be noted that a copolymer which contains such a diluent comonomer and a reactive comonomer capable of reacting at a surface to provide covalent binding to a surface may be used to coat a hydrophilic surface, the reactive comonomer roviding binding to the surface and the diluent modifying hysical and mechanical properties. However, such a copolymer may also be to coat hydrophobic surfaces, in which the "diluent" monomer will act as a comonomer capable of binding to the surface by physisorption and the comonomer capable of covalent binding will act as a crosslinkable comonomer.

According to a feature of the present invention polymers of the invention may be prepared by:

a) copolymerising a comonomer containing a group bearing a centre of permanent positive charge, preferably a zwitterionic group, a comonomer containing a group capable of stably binding the polymer to a surface and optionally a diluent and/or crosslinkable comonomer; or b) polymerising a monomer containing a group containing a group bearing a centre of permanent positive charge, preferably a zwitterionic group, and a group capable of stably binding the polymer to a surface and optionally further comonomer containing a group capable of stably binding the polymer to the surface and a diluent and/or a crosslinkable comonomer.

Any conventional technique may be used for polymerisation, typically thermal or photochemical polymerisation. Where comonomers capable of producing crosslinking in the coated polymer film are present, the polymerisation condition are set such that crosslinking does not occur during polymerisation. Thus, for example, actinic radiation would not be used to prepare a polymer containing a comonomer which can form crosslinks by exposure to actinic radiation.

For thermal polymerisation a temperature from 40 to 100° C., typically 50° to 80° C. is used. For photochemical polymerisation actinic radiation such as gamma, U.V., visible, or microwave radiation may be used. Typically U.V. radiation of wavelength 200 to 400 nm is used.

The polymerisation is generally performed in a reaction medium, which is for instance a solution or dispersion using as a solvent for example acetonitrile, dimethyl formamide, chloroform, dichloromethane, ethyl acetate, dimethyl sulphoxide, dioxan, benzene, toluene, tetrahydrofuran, or where the polymer does not contain groups which react with protic solvents, water or an alkanol containing from 1 to 4 carbon atoms, e.g. methanol, ethanol or propan-2-ol. Alternatively, a mixture of any of the above solvents may be used.

The polymerisation may be carried out in the presence of one or more polymerisation initiators, such as benzoyl peroxide, 2,2'-azo-bis(2-methylpropionitrile) or benzoin methyl ether. Other polymerisation initiators which may be used are disclosed in "Polymer Handbook", 3rd edition, Ed. J. Brandrup and E. H. Immergut, Pub. Wiley-Interscience, New York, 1989.

Generally the copolymerisation is performed for 1 to 72 hours, preferably 8 to 48, for instance 16 to 24 hours, and under an inert atmosphere of for example nitrogen or argon. The polymer is generally purified by dialysis, precipitation in a non-solvent (e.g. diethyl ether or acetone) or ultrafiltration. The resulting polymer is generally dried under vacuum, eg. for 5 to 72 hours and has a molecular weight from 10,000 to 10 million, preferably from 20,000 to 1 million.

The precise proportion and nature of the various comonomers used to prepare a copolymer according to the present invention comprising residues of a comonomer containing a group bearing a centre of permanent positive charge and a comonomer containing a group capable of stably binding the polymer to a surface may be adjusted to provide a copolymer which is particularly suitable for coating a particular surface. Thus the proportion of comonomer containing a group capable of stably binding the polymer to a surface may be adapted to provide efficient physisorption at a particular hydrophobic surface, to correspond to the number of functional groups at a particular surface or to provide efficient binding by ionic interaction with a particular surface. Similarly the proportion of the comonomer containing a group bearing a centre of permanent positive charge and of diluent and/or crosslinkable comonomer may be adapted to provide the desired biocompatibility and physical and mechanical properties. It will be appreciated that to obtain the desired combination of properties more than one type of comonomer containing a group bearing a centre of permanent positive charge, comonomer containing a group capable of stably binding the polymer to a surface or crosslinkable and/or diluent comonomer may be used.

Similarly, in polymers comprising residues of a monomer containing a group bearing a centre of permanent positive charge and a group capable of stably binding the polymer to a surface, the nature of these groups may be adjusted to provide the desired biocompatibility and efficient binding at a particular surface, as well as desired physical and mechanical properties. Where, in addition, a diluent and/or crosslinkable comonomer is used the nature of the diluent and/or crosslinkable comonomer and the proportions of the comonomers may be likewise adjusted. It will again be appreciated that to obtain the desired combination of properties more than one type of monomer containing a group bearing a centre of permanent positive charge and a group capable of stably binding the polymer to a surface and/or more than one type of crosslinkable and/or diluent comonomer may be used.

The monomer composition which is subjected to polymerisation to provide a polymer according to the invention comprises a minimum of 0.01%, preferably 1%, more preferably 5% by weight of monomer or monomers containing a group bearing a centre of permanent positive charge and a maximum of 99.9%, preferably 99%, more preferably 95% by weight of other monomer or monomers. Such other monomer or monomers may be a monomer or monomers containing a group capable of stably binding the polymer to a surface, a diluent monomer or monomers and/or a crosslinkable monomer or monomers.

The monomer composition further comprises a minimum of 0.01%, preferably 1%, more preferably 5% by weight of monomer or monomers containing a group capable of stably binding the polymer to a surface and a maximum of 99.9%, preferably 99%, more preferably 95% by weight of other monomer or monomers. Such other monomer or monomers may be a monomer or monomers containing a group bearing a centre of permanent positive charge, a diluent monomer or monomers and/or a crosslinkable monomer or monomers.

It will be appreciated that where at least some of the monomer or monomers containing a group bearing a centre of permanent positive charge also contains a group capable of stably binding the polymer to a surface, at least a proportion of the content of both these groups is provided by the same monomer. In such a case the polymer may be a homopolymer of a monomer containing both these groups.

Where the polymer is to bind to a surface by physisorption then preferably the monomer composition comprises no more than 95%, more preferably no more than 90% and even more preferably no more than 80% by weight of monomer or monomers containing an alkyl, fluoroalkyl or siloxane group which is capable of binding the polymer to a surface by physisorption and which does not also contain a group bearing a centre of permanent positive charge, the balance of the composition being monomer or monomers containing a group bearing a centre of permanent positive charge, diluent monomer or monomers and/or crosslinkable monomer or monomers. Such a composition typically comprises up to 50% by weight of diluent comonomer or comonomers. Where diluent comonomer is present, it preferably comprises at least 1t, more preferably 5%, by weight of the total comonomer composition. Where present, crosslinkable comonomer or comonomers generally comprise from 0.1% to 20% by weight of the total comonomer composition.

Where different comonomers are used to provide the centre of permanent positive charge and the physisorption, then preferably the molar ratio in the copolymer of comonomer residues bearing a centre of permanent positive charge to comonomer residues containing an alkyl, fluoroalkyl or siloxane group capable of binding the polymer to a surface by physisorption is from 5:95 to 80:20, more preferably 10:90 to 50:50. In addition the copolymer preferably comprises from 5% to 50%, more preferably 10% to 25%, by mole residues of diluent monomer and/or from 0.1 to 20%, more preferably 1% to 10%, by mole residues of crosslinkable comonomer, provided that where residues of both diluent and crosslinkable comonomer are present, they do not exceed in combination 50%, preferably 35% by mole.

Where the polymer is to bind covalently to a surface then preferably the monomer composition comprises no more than 25%, more preferably up to 20% and even more preferably up to 15% by weight of monomer or monomers containing a group capable of binding the polymer to a surface covalently and which does not also contain a group bearing a centre of permanent positive charge; the balance of the composition being monomer or monomers containing a group bearing a centre of permanent positive charge, and optionally diluent monomer or monomers. Such a composition typically comprises up to 95%, preferably to 90%, by weight of diluent comonomer or comonomers. Where diluent comonomer is present, it preferably comprises at least 5%, more preferably 10%, by weight of the total comonomer composition.

Preferably the molar ratio in the copolymer of comonomer residues bearing a centre of permanent positive charge to comonomer residues containing a reactive group capable of binding the polymer to a surface by covalent bonding is from 5:95 to 95:5, more preferably 50:50 to 90:10. In addition, the copolymer preferably comprises from 5% to 50%, more preferably 10% to 25%, by mole residues of diluent monomer and/or from 0.1% to 20%, more preferably 1% to 10%, by mole residues of crosslinkable comononer, provided that where residues of both diluent and crosslinkable comonomer are present, they do not exceed in combination 50%, preferably 35% by mole.

Where the polymer is to bind to a surface by ionic interaction, then preferably the molar ratio in the copolymer of comonomer residues bearing a centre of permanent positive charge to comonomer residues containing an ionic group capable of binding the polymer to a surface by ionic interactions is from 5:95 to 95:5, more preferably 50:50 to 90:10. In addition, the copolymer preferably comprises from 5% to 50%, more preferably 10% to 25%, by mole residues of diluent monomer and/or from 0.1% to 20%, more preferably 1% to 10%, by mole residues of crosslinkable comonomer, provided that where residues of both diluent and crosslinkable comonomer are present, they do not exceed in combination 50%, preferably 35% by mole.

In addition the monomer or comonomer composition may comprise further components such as a polymerisation initiator, chain transfer agent, acid, base, surfactant, emulsifier or catalyst of conventional type each in an amount from 0.1% to 5%, typically from 0.2% to 3% and preferably about 0.5%, by weight each relative to the total weight of the monomers.

As a further feature the present invention provides a process for biocompatibilising a surface which comprises coating the surface with a polymer according to the present invention. Various types of surfaces may be coated depending upon the nature of the groups in the polymer capable of binding it to the surface.

Polymers containing residues of monomers containing alkyl, fluoroalkyl or siloxane groups capable of binding the polymer to a surface by physisorption are particularly suitable for coating hydrophobic surfaces, e.g. polyethylene, polypropylene and polytetrafluoroethylene (PTFE) surfaces; fluorine containing polymers of the invention being particularly suited to coating PTFE surfaces.

Hydrophilic surfaces may be rendered hydrophobic and suitable for coating with such polymers by known methods (see for example "Chemical Reactions of Polymers" Ed. E. M. Fettes, 1964, Interscience, London).

Treatment with such a polymer is generally carried out by coating the surface with a solution, dispersion (including a microdispersion) of the polymer, generally in an alcoholic, aqueous, organic or halogenated solvent or a mixture thereof, e.g. methanol, ethanol, dichloromethane or freon. The treatment is generally carried out at ambient or elevated temperature, such as from 5° to 60° C.

In one specific embodiment of the invention, the copolymer is coated onto the substrate in the form of a microdispersion for example a microemulsion.

After coating the polymer may be crosslinked if it contains the residues of crosslinkable comonomer by known method for crosslinking the specific crosslinkable groups which are present. Crosslinking may, for instance, be introduced thermally, using actinic radiation, using reactive gases for example ammonia by changing the pH, using difunctional additives or by using activation chemistries for example by known methods as described in "Methods in Enzymology, volume 135, Immobilised Enzymes and Cells, part B", Ed. K. Mosbach, Academic Press Inc. New York, 1987. This activation may be performed on the dry coating, in the cases of thermal radiation or gas treatment. Alternatively for cases where the pH needs to be changed or additives need to be included, activation may be performed on the coated material in a solution which does not remove the coating.

Surfaces having functional groups such as hydroxyl, carboxyl or amino groups are particularly suitable for treatment with polymers according to the invention comprising residues of monomer containing a group capable of binding the polymer to a surface covalently.

Where necessary the surface of the substrate may be functionalised prior to treatment. For surfaces which do not have functional groups it is necessary to introduce these groups at the surface before treatment with the polymer. This can be effected by known etching or derivatising techniques, such as plasma discharge, which introduce the appropriate surface functionality (see for example "Chemical Reactions of Polymers" Ed. E. M. Fettes, 1964, Interscience, London).

In certain cases it is also necessary to activate functional groups at the surface of the substrate and/or the reactive groups of the polymer of the invention. This may be achieved by known means using a known activating agent for example a carbodiimide such as 1-ethyl-3-(3-dimethylaminopropyl)carbodiimide. Other suitable activating agents are disclosed in "Methods in Enzymology", supra. It will be appreciated that corresponding methods of activation of groups on a polymer may also be used to attach moieties, such as ligands to the polymer when coated on a substrate.

Treatment with such a polymer is generally carried out by treating the surface with a solution of the polymer, generally an alcoholic, aqueous alcoholic or aqueous solution. The treatment is generally carried out at a temperature from −5° to 50° C., for from 0.1 to 24 hours and at a pH from 2 to 13.

Surfaces having ionic groups such as carboxyl, sulphonate, phosphate, ammonium or phosphonium groups are particularly suitable for treatment with polymers according to the invention comprising residues of monomer containing a group capable of binding the polymer to ionic interaction.

Where necessary the surface of the substrate may be functionalised prior to treatment. For surfaces which do not have ionic groups it is necessary to introduce these groups at the surface before treatment with the polymer. This can be effected by known etching or derivatising techniques, such as plasma discharge, which introduce the appropriate surface functionality (see for example "Chemical Reactions of Polymers" Ed. E. M. Fettes, 1964, Interscience, London)

Treatment with such a polymer is generally carried out by treating the surface with a solution of the polymer, generally an alcoholic, aqueous alcoholic or aqueous solution. Treatment is generally carried out at a temperature from −5° to 50° C., for from 0.1 to 24 hours and at a pH from 2 to 13.

Materials may be coated with polymers of the invention by known techniques, such as dip-coating, spray-coating, web-coating or spin coating.

Materials having surfaces coated according to the present invention can be used as a construction material for implants or prostheses for the human or animal body, particularly where these implants or prostheses are to come into direct physical contact with blood and where biocompatibility and particularly haemocompatibility are required e.g. in heart valves. They can also be used in the construction of membranes and other devices that are to be brought into contact with blood or other body fluids on an extra-corporeal basis, for example in heart-lung machines or artificial kidneys.

Additionally the polymers of the invention can be used to coat materials employed in down stream processing applications e.g. separation membranes and process equipment and tubing. In particular the materials of the invention can be used to modify the surface properties of biofiltration membranes in bioreactors and fermentation systems, where the membranes come into direct contact with complex biological solutions containing e.g. proteins, polysaccharides, fats and even whole cells. The polymers of the invention are particularly useful in reducing membrane fouling by the components of a process solution.

When the polymers of the present invention are used to coat the surface of a material which is then used in the construction coat of finished devices, it may be necessary to take precautionary steps to ensure that the coated surface is not damaged and the effectiveness of the treatment reduced before the finished device is produced.

In addition, the polymers of the present invention can be used to coat finished implants, prostheses, membranes, catheters, contact lenses, intraocular lenses, and other devices which are coated with a polymer according to the present invention to impart biocompatibility to the article.

The invention thus also provides a finished device comprising a surface having a coating thereon of a polymer of the present invention.

FIG. 1 compares scanning electron micrographs of a polyimide sheet treated and untreated with a copolymer of the invention and then contacted with blood. FIG. 1. (a) shows a scanning electron micrograph (1200×) of an unsubbed, untreated poly(imide) sheet. FIG. 1. (b) shows a scanning electron micrograph (900×) of a poly(acrylic acid) subbed poly(imide) sheet treated with poly (2(methacryloyloxyethyl)-2(trimethylammonium)ethyl phosphate-co-2-aminomethacrylate) (9:1), in accordance with Example 8.

The present invention will now be further illustrated by the following Examples:

EXAMPLES

The following assays have been used to evaluate coatings of polymers according to the present invention.
Protein adsorption using an enzyme immunoassay The assay determines adsorption of human fibrinogen at a surface. This protein is representative of protein which is typically adsorbed at a surface. The assay can be readily modified to determine the adsorption of other proteins.

Discs (7 mm in diameter) of untreated material (as controls) and material treated with polymer as described below, were prepared and washed with phosphate buffered saline (PBS) for at least 10 minutes in the wells of microplates. The samples were incubated with human plasma (300 µl) for 10 minutes and then washed with PBS three times. Each of the test samples and each of the control samples were treated with human fibrinogen-specific antibody (300µl) for 30 minutes and again washed with PBS three times. As a control for non-specific binding of antibody to the samples, each sample was also incubated with non-specific antibody (300 µl) for 3.0 minutes. A conjugate of horseradish peroxidase and a second antibody specific to the first antibody (300 µl) was added to both the test samples and the controls and incubated for 30 minutes before washing. Each of the test samples and the controls were transferred to new microplates and a solution of 2,2'-azino-bis(3-ethyl benzthiazoline-6-sulphonic acid) (ABTS) in phosphate-citrate buffer (300 µl,0.6 mg/ml) added, the reaction was allowed to proceed for 10 minutes. At this time an aliquot of the mixture (200 µl) was removed and added to a solution of citric acid and sodium azide in distilled water (20 µl, 0.21 g/ml and 2 mg/ml respectively). The optical density of the solutions was measured using a Techgen automated plate reader at 650 nm using the ABTS solution as blank.

In an alternative procedure, rather than using ABTS, each of the samples was transferred to wells of new microplates and a solution of o-phenylene diamine (OPD) in phosphate-citrate buffer (300 µl, 0.4 mg/ml) added, and the reaction was allowed to proceed for 10 minutes. At this time an aliquot of the mixture (200 µl) was removed from each well and the optical density of the solutions was measured using a Techgen automated plate reader at 450 nm using the OPD solution as blank.
Activated Platelet Study Blood was collected from a healthy adult volunteer using the double syringe method where the first 5 ml of blood is discarded. The blood was collected into tri-sodium citrate (32 g/l) in the proportion of 9 volumes to 1 volume citrate in plastic tubes. The samples were kept at room temperature on a spiral mixer until used.

Discs (7 mm in diameter) of untreated material as controls and material treated with polymers as described below were prepared and placed into the wells of a microplate. The samples were incubated with whole fresh citrated blood (200 µl) on a rotary mixer for 30 minutes before washing in PBS four times. Platelet activation was measured by a proprietary assay (Lindon, J. N. et al., *Blood*, 68, 355 (1986)) and British Patent Application No. 91-25721.2].

In an alternative procedure half of the test replicates were incubated with citrated blood (200 µl) and the remainder were incubated with EDTA-treated blood on a phase shaker for 30 minutes before washing in PBS four times. Platelet activation was measured in a manner similar to that described above for detection of proteins by enzyme immunoassay using antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.
C-Reactive protein (CRP) binding assay C reactive protein is a protein which binds specifically to isolated ammonium phosphate esters groups e.g. phosphoryl choline groups which are attached to a surface.

Discs (7 mm in diameter) of untreated material and material treated with polymer as described below, were prepared and washed with HEPES-buffered saline (HBS) for a least 10 minutes in the wells of microplates. The samples were incubated in quadruplet for 45 minutes in a protein solution consisting of bovine serum albumin (BSA) (40 mg/ml) and CRP (0.012 mg/ml) in HBS and containing calcium chloride (1 mM). In parallel, identical samples (both coated and uncoated) were incubated either in BSA/$Ca^{2+}$ solution in the absence of CRP, in BSA/CRP/$Ca^{2+}$ solution in the presence of soluble phosphoryl choline (1.5 mg/ml) or in BSA/CRP solution containing EDTA (20 mM) rather than calcium chloride.

After incubation, all the samples were washed in phosphate buffered saline (PBS) three times and then incubated for 1 hour in $^{300}$ μl of a 1:100 dilution of commercially available anti-CRP antibody conjugated with horseradish peroxidase. The samples were washed three times in PBS as before and transferred to new microplates. A solution of o-phenylene diamine (OPD, 0.4 mg/ml) in phosphate-citrate buffer was added and the reaction allowed to proceed for ten minutes. At this time an aliquot of the mixture (200 μl) in each of the wells was transferred to a new well, and the optical density of the solutions measured using a Techgen automated plate reader at 450 nm using the OPD solution as a blank.

A positive control containing isolated phosphoryl choline groups may be provided using beaded agarose immobilised with p-aminophenylphosphoryl choline. The specificity of CRP binding may be demonstrated by inhibition by phosphoryl choline and dependance upon the presence of calcium.

EXAMPLE 1

Preparation of poly(2(methacryloyloxyethyl)-2' (trimethylammonium)ethyl phosphate inner salt -co- n-dodecyl methacrylate (1:2)

2 (Methacryloyloxyethyl) -2'(trimethylammonium) ethyl phosphate inner salt (5.0 g, 0.0170 mole) and n-dodecylmethacrylate (8.55 g, 0.0340 mole) were dissolved in methanol/THF (140 ml, 5:9). The solution was stirred (250 rpm) at 23° C. under a stream of nitrogen (50 ml/min) for 30 minutes. 2,2'-Azo-bis(2-methylpropionitrile) (0.17 g, 1.02 mmole) was added and the flow of nitrogen was reduced to 10 ml/min, the temperature was raised to 60° C. This temperature and nitrogen flow rate were maintained for 16 hours.

The mixture was allowed to cool and vacuum filtered. The filtrate was collected and the polymer precipitated by dropwise addition to acetone (1.21).

The polymer was isolated by filtration under vacuum under a nitrogen atmosphere and finally dried under reduced pressure overnight at room temperature. The resulting polymer (9.5 g,70%) was a fine white powder.

In an alternative procedure, 2(methacryloyloxyethyl)-2' (trimethylammonium)ethyl phosphate inner salt (12.06 g, 0.0409 mole) and n-dodecyl methacrylate (20.52 g, 0.0808 mole) were dissolved in propan-2-ol (215 ml) and ethyl acetate (85 ml). The solution was stirred (250 rpm) at 23° C. under a stream of nitrogen (50 ml/min) for 30 minutes, 2,2'-azo-bis(2-methylpropionitrile) (0.0645 g, 0.39 mmole) was added and the flow of nitrogen was reduced to 10 ml/min, the reaction temperature was raised to 60° C. This temperature and nitrogen flow rate were maintained for 40 hours.

The mixture was allowed to cool and vacuum filtered. The filtrate was evaporated to dryness using a rotary evaporator and dissolved in dichloromethane (120 ml) and methanol (10 ml). The polymer was isolated from this mixture by precipitation in acetone (2500 ml), vacuum filtration and drying. The polymer was redissolved in dichloromethane (100 ml) and methanol (30 ml) and isolated as described above.

The resulting polymer, obtained in 70–80% yield was a white powder.

NMR(200 MHz, d, ppm, $CD_3OD/CDCl_3$) 4.2–4.4 (b), 3.8–4.2 (b), 3.6–3.8 (b), 3.3 (s), 1.8–2.2 (b), 1.5–1.8 (b), 1.2–1.5 (s), 0.8–1.0 (s)

IR($cm^{-1}$, KBr disc) 3430, 2929, 2854, 1732, 1469, 1246, 1156, 1089, 968, 788.

| Elemental Analysis | | | | |
|---|---|---|---|---|
| theory | C 64.5, | H 9.9, | N 1.8, | P 3.9 |
| actual | C 59.0, | H 10.0, | N 1.8, | P 3.9 |

The polymer had a relative viscosity in ethanol: chloroform (50:50) at 25° C. of 1.13±0.02 (when prepared using methanol: THF as solvent) and 1.26±0.02 (when prepared using propan-2-01: ethylacetate as solvent).

EXAMPLE 2

The coating of poly(ethylene) ribbon with poly(2 (methacryloyloxyethyl)-2'(trimethylammonium) ethyl phosphate inner salt -co- n-dodecyl methacrylate (1:2)

Poly(ethylene) ribbon was washed with ethanol and allowed to dry in the air. The poly(2(methacryloyloxyethyl) -2'(trimethylammonium)ethyl phosphate inner salt -co- n-dodecyl methacrylate) (1:2) (5Omg) was dissolved in ethanol/chloroform (5 ml, 40:1) and the poly(ethylene) coated by a one stage mechanical dip-coating procedure drawing the ribbon through the solution slowly. The coated ribbon was allowed to dry in a dust free atmosphere at room temperature.

The treated poly(ethylene) showed a 65% reduction in protein adsorption as compared to the untreated material and a 83% reduction in platelet activation (determined using the assay of Lindon et al) as compared to the untreated material.

In the C-reactive protein binding assay, no binding of CRP was observed to the treated poly(ethylene). In contrast, CRP binding was observed for a positive control. The specificity of this CRP binding was demonstrated by the fact that it was inhibited by phosphoryl choline and dependence upon the presence of calcium.

According to an alternative procedure, polyethylene ribbon was washed in propan-2-ol and coated with the copolymer dissolved in propan-2-ol (1 g in 100 ml) at 40° C. using an otherwise analogous manner.

EXAMPLE 3

In an analogous manner to that described in Example 2 steel and PVC substrates were coated with poly(2 (methacryloyloxyethyl) -2'(trimethylammonium) ethyl phosphate inner salt -co-n-dodecyl methacrylate (1:2).

The treated steel samples showed a reduction in protein adsorption of over 80% compared to untreated samples and the treated PVC samples showed a reduction in protein adsorption of over 70% compared to untreated samples as measured by the enzyme immunoassay described above. In a further determination a sample of stainless steel coated with the polymer showed a reduction, compared to untreated material, in protein adsorption of 84% as determined by the enzyme immunoassay technique and a reduction of 95% in platelet activation as determined by the platelet activation assay described above using anti-GMP140. A further sample of PVC coated with the polymer showed a reduction of 87% in protein adsorption and a reduction of 100% in platelet activation, compared to untreated material, using the same assay techniques.

EXAMPLE 4

Preparation of poly(2(methacryloyloxyethyl)-2' (trimethylammonium)ethyl phosphate inner salt-co- n-dodecyl methacrylate (1:4)

2 (Methacryloyloxyethyl) -2'(trimethylammonium) ethyl phosphate inner salt (10.00 g, 0.0339 mole) and n-dodecyl methacrylate (35.56 g, 0.1400 mole) were dissolved in propan-2-ol (200 ml) and ethyl acetate (200 ml). The solution was stirred (250 rpm) at 23° C. under a stream of nitrogen (50 ml/min) for 30 minutes. 2,2'-azo-bis-(2-methylpropionitrile) (0.0886 g, 0.54 mmole) was added and the flow of nitrogen was reduced to 10 ml/min, the reaction temperature was raised to 60° C. This temperature and nitrogen flow rate were maintained for 40 hours.

The mixture was allowed to cool and vacuum filtered. The filtrate was evaporated to dryness using a rotary evaporator and dissolved in dichloromethane (130 ml). The polymer was isolated from this mixture by precipitation in acetone (2500 ml), vacuum filtration and drying. The polymer was redissolved in dichloromethane (120 ml) and methanol (10 ml) isolated as before.

The resulting polymer, obtained in 70–80% yield was a white solid.

NMR(200 MHz, d, ppm, CD$_3$OD/CDCl$_3$) 4.2–4.4 (b), 3.8–4.2 (b), 3.6–3.8 (b), 3.3 (s), 1.8–2.2 (b), 1.5–1.8 (b), 1.2–1.5 (s), 0.8–1.0 (s)

IR(cm$^{-1}$, KBr disc) 3430, 2929, 2854, 1732, 1469, 1246, 1156, 1089, 968, 788.

| Elemental Anaylsis: | | | | |
|---|---|---|---|---|
| theory | C 68.9, | H 10.5, | N 1.1, | P 2.4 |
| actual | C 65.5, | H 10.8, | N 1.1, | P 2.4 |

The polymer had a relative viscosity in ethanol: chloroform (50.50) at 25° C. of 1.26±0.02.

Samples of polyethylene, steel and PVC were coated using the methods described in Examples 2 and 3. Using the enzyme immunoassay for protein adsorption, a greater than 80% reduction in protein adsorption on steel and greater than 70% reduction in protein adsorption on PVC were obtained.

In a further determination, a sample of stainless steel coated with the polymer showed a reduction of 80% in protein adsorption (determined by the enzyme immunoassay described above) and a reduction of 95% in platelet activation (determined by the platelet activation assay described above using anti-GMP 140), compound to untreated material. A sample of PVC coated with the polymer showed a reduction of 70% in protein adsorption and 100% in platelet activation compound to untreated material using the same assay techniques.

EXAMPLE 5

Preparation of poly(2(methacryloyloxyethyl)-2' (trimethylammonium)ethyl phosphate inner salt-co- 1H, 1H, 2H,2H,heptadecafluorodecyl methacrylate (2:1)

2(methacryloyloxyethyl)-2'(trimethylammonium)ethyl phosphate inner salt (1.0 g, 0.0034 mole) and 1H, 1H, 2H, 2H-heptadecafluorodecyl methacrylate (0.90 g, 0.0017 mole) were dissolved in methanol (10 ml) and tetrahydrofuran (10 ml). The solution was stirred (250 rpm) at 23° C. under a stream of nitrogen (50 ml/min) for 30 minutes. 2,2'-azo-bis(2-methylpropionitrile) (0.0167 g, 0.1ommole) was added and the flow of nitrogen was reduced to 10 ml/min, the reaction temperature was raised to 60° C. This temperature and nitrogen flow rate were maintained for 16 hours.

The mixture was allowed to cool and vacuum filtered. The filtrate was evaporated to dryness using a rotary evaporator and dissolved in dichloromethane (10 ml) and methanol (10 ml). The polymer was isolated from this mixture by precipitation in acetone (500 ml), vacuum filtration and drying. The polymer was redissolved in dichloromethane (10 ml) and methanol (10 ml) and isolated as before. The resulting polymer, obtained in 70–80% yield was a white powder.

NMR(200 MHz, d, ppm, CD$_3$OD/CDCl$_3$) 4.2–4.4 (b), 3.8–4.2 (b), 3.6–3.8 (b), 3.3 (s), 2.4–2.7(b), 2.2–1.7(b), 1.2–1.0(b), 0.8–1.0 (b)

The polymer was used to coat a polyvinylidene fluoride microfiltration membrane. The resulting coated membrane showed very little flux decline during processing with bovine serum albumin (BSA) indicating very little protein fouling. The flux change for the treated membrance was from 6000 to 5000 l/m$^2$/hr compared to the flux change for the untreated membrane which was from 5000 to 500 l/m$^2$/hr. Both measurements were taken over a two hour period.

EXAMPLE 6

Preparation of poly(2(methacrylovloxyethyl)- 2'trimethylammonium) ethyl phosphate inner salt- co-n-hexadecyl methacrylate (1:2)

2 (methacryloyloxyethyl) -2'(trimethylammonium) ethyl phosphate inner salt (2.00 g, 6.78 mmole) and n-hexadecyl methacrylate (4.21 g, 0.0136 mole) were dissolved in propan-2-ol (35.5 ml) and ethyl acetate (14.5 ml). The solution was stirred (250 rpm) at 23° C. under a stream of nitrogen (50 ml/min) for 30 minutes. 2,2'-azo-bis(2-methylpropionitrile) (0.0168 g, 0.10 mmole) was added and the flow of nitrogen was reduced to 10 ml/min, the reaction temperature was raised to 60° C. This temperature and nitrogen flow rate were maintained for 40 house.

The mixture was allowed to cool and vacuum filtered. The filtrate was evaporated to dryness using a rotary evaporator and dissolved in dichloromethane (10 ml) and methanol (10 ml). The polymer was isolated from this mixture by precipitation in acetone (700 ml), vacuum filtration and drying. The polymer was redissolved in dichloromethane (10 ml) and methanol (10 ml) isolated as described above. The resulting polymer, obtained in 40–60% yield was a white solid.

NMR(200 MHz, d, ppm, CD$_3$OD/CDCl$_3$) 4.2–4.4 (b), 3.8–4.2 (b), 3.6–3.8 (b), 3.3 (s), 1.8–2.2 (b), 1.5–1.8 (b), 1.2–1.5 (s), 0.8–1.0 (s).

IR(cm$^{-1}$, KBr disc) 3430, 2929, 2854, 1732, 1469, 1246, 1156, 1089, 968, 788.

EXAMPLE 7

Preparation of poly(2(methyacryloyloxyethyl)-2 (trimethyl-ammonium)ethyl phosphate inner salt -co- 2-aminoethyl-methacrylate) (9:1)

2(Methacryloyloxyethyl)-2(trimethylammonium)ethyl phosphate inner salt (9.96 g, 0.0335 mole) was dissolved in methanol (115 ml). Water (10 ml) was added followed by the addition of 2-aminoethylmethacrylate (0.5571 g, 0.0034 mole). The solution was stirred (250 rpm) at 22° C. under a stream of nitrogen (70 ml/min) for 30 minutes. 2,2'Azo-bis (2-methylpropionitrile) 0.12 g, 0.73 mmole) was added and the flow of nitrogen was reduced to 9 ml/min, the temperature was raised to 60° C. The temperature and nitrogen flow rate were maintained for 16 hours.

The mixture was allowed to cool and transferred to centrifuge tubes. The samples were centrifuged for 30 minutes at 4000 rpm. The samples were combined and the polymer precipitated by dropwise addition to acetone (800 ml). The acetone was decanted from the polymer and the polymer washed with acetone (200 ml). The polymer was isolated by vacuum filtration under a nitrogen atmosphere and finally dried in vacuo overnight at room temperature.

IR ($cm^{-1}$;KBr disc) 3435, 2929, 2096, 1732, 1628, 1245, 1166, 1089, 970.

EXAMPLE 8

Treatment of poly(acrylic acid) subbed poly(imide) sheets with poly(2(methacryloyloxyethyl)-2 (trimethylammonium) ethyl phosphate inner salt -co- 2-aminoethylmethacrylate) (9:1).

Poly(imide) samples were placed in the plasma chamber of a plasma barrel etcher and evacuated with a pump down to a pressure of 0.001 mbar. Oxygen was then allowed to flow into the reactor. The plasma was started with 90 W forward power and nearly 0W backward. The pressure was approximately 0.7 mbar. The plasma was turned on for 5 minutes, then the radio frequency generator (13.56 MHz) was switched off at the same time as the flow of oxygen stopped. The pressure was allowed to drop and the valve of the flask with acrylic acid was opened to let the monomer flow into the chamber (100% acrylic acid). The vacuum was decreased to 0.3 mbar. The high frequency generator was then started with 30W forward power and 0W backward power and the polymerisation carried out for 20 minutes. After switching off the high frequency generator and closing the valve to the acrylic acid, the chamber was evaporated again for another 5 minutes to remove all of the excess monomer.

The poly(acrylic acid) subbed poly(imide) was cut into $4 \times 1.5 cm^2$ pieces and washed with distilled water. The squares were then added to a 1.25% solution (6.3 ml) of poly(2(methacryloyloxyethyl)-2(trimethylammonium) ethyl phosphate inner salt -co- 2-aminoethylmethacrylate (9:1). 1-Ethyl-3(3-dimethylaminopropyl)carbodiimide (20 g) was then dissolved in the solution and the pH then adjusted to 5.0 using hydrochloric acid (0.5M). After 1 hour the samples were removed, washed with distilled water and allowed to dry.

Visualisation of Platelet Activation on a Surface

Blood was collected from a healthy adult volunteer using the double syringe method where the first 5 ml of blood is discarded. The blood was collected into tri-sodium citrate (32 g/1) in the proportion of 9 volumes of blood to 1 volume citrate in plastic tubes. The samples were kept at room temperature on a spiral mixer until used.

1 $cm^2$ samples of poly(2(methacryloyloxyethyl)-2- (trimethylammonium)ethyl phosphate inner salt -co- 2-aminoethylmethacrylate) (9:1) coated poly(imide) as prepared above and of uncoated poly(imide) as a comparison were placed into 1 ml of the fresh citrated blood and incubated for 30 minutes on a spiral mixer at room temperature. The samples were then washed in phosphate buffered saline (PBS,pH7.4) prior to fixing in an aliquot of the following solution for 30 minutes.

2 ml 25% w/v glutaraldehyde 83 ml 0.15M PBS (pH7.4)

15 ml Saturated picric acid.

Picric acid increases the preservation of lipid-associated protein. The samples were again washed in PBS and then dehydrated using 70% and 100% methanol followed by 100% acetone prior to drying in air. Finally samples were sputter-coated with a platinum target (20 mAmps for 6×30 seconds) and observed at appropriate magnifications using a scanning electron microscope.

No platelet activation was seen on the coated poly(imide) samples whereas gross adhesion activation and aggregation were seen on the uncoated sample (see FIG. 1). The presence of the polymer on the surface was confirmed by the use of X-ray photoelectron spectroscopy (XPS). It can thus be seen that treatment of polyamide by first coating with a subbing layer of acrylic acid to render the surface reactive, and then coating with a copolymer according to the present invention substantially removed the haemostatic reaction to the polyamide.

EXAMPLE 9

Preparation of poly(2(methacryloyloxyethyl)-2' (trimethylammonium) ethyl phosphate inner salt-co- 3-chloro-2-hydroxypropyl methacrylate (1:1)

2(methacryloyloxyethyl)-2'(trimethylammonium)ethyl phosphate inner salt (7.46 g, 25.3 mmole), 3-chloro-2-hydroxypropyl methacrylate (4.51 g, 25.3 mmole) and p-toluene sulphonic acid monohydrate (0.1048 g, 0.55 mmole) were dissolved in methanol (101 ml). The solution was stirred (250 rpm) at 23° C. under a stream of nitrogen (50 ml/min) for 30 minutes. 2,2'-azo-bis(2-methylpropionitrile) (0.0843 g, 0.51 mmole) was added and the flow of nitrogen was reduced to 10 ml/min, the reaction temperature was raised to 60° C. This temperature and nitrogen flow rate were maintained for 16 hours.

The polymer was isolated from this mixture by precipitation in acetone (1500 ml), vacuum filtration and drying. The polymer was redissolved in methanol (40 ml) and isolated as before using acetone (1000 ml).

The resulting polymer, obtained in 62% yield was a white solid.

NMR(200 MHz, d, ppm, $CD_3OD/CDCl_3$) 4.2–4.4 (b), 4.3–4.0 (b), 3.6–3.8 (b), 3.3 (s), 1.6–2.4(b), 1.0–1.5(b), 0.7–1.0(b).

IR($cm^{-1}$, KBr disc) 3416, 2959, 1727, 1655, 1490, 1247, 1165, 1088, 968, 792, 748.

EXAMPLE 10

Preparation of poly(2(methacryloyloxyethyl)-2' (trimethylammonium)ethyl phosphate inner salt -co- 7 dodecynmethacrylate (1:2)

The polymer was prepared by a method analogous to that described in Examples 4 and 6 using 2(methacryloyloxyethyl)-2'(trimethylammonium)ethyl phosphate inner salt (8.41 g, 0.0285 mole) and n-dodecynmethacrylate (14.31 g, 0.0572 mole) dissolved in propan-2-ol (160 ml) and ethyl acetate (60 ml).

The resulting polymer, obtained in 35% yield was a white powder.

NMR(100 MHz,d,ppm,CD$_3$OD/CDCl$_3$)4.2–4.4(b), 3.8–4.2(b),3.6–3.8(b),3.3(s),2.25(s),1.8–2.2(b),1.5–1.8(b), 1.2–1.5(s),0.8–1.0(s)

IR(cm$^{31\ 1}$,KBr disc) 3430, 2929, 2854, 1732, 1469, 1246, 1156, 1089, 968, 788.

| Elemental Analysis | | | | |
|---|---|---|---|---|
| theory | C 65.1 | H 9.0 | N 1.8 | P 3.9 |
| actual | C 54.9 | H 8.5 | N 1.9 | P 4.4 |

Relative Viscosity (chloroform/ethanol 50:50, 30° C.) 1.18.

The polymer may be crosslinked by gamma-irradiation or exposure to UV light which renders the polymer insoluble in dichloromethene/methanol.

A sample of stainless steel treated with the polymer showed a reduction in protein adsorption of 68% (determined by the enzyme immunoassay described above) and a reduction in platelet activation of 100% (determined by the platelet activation assay described above, using anti GMP 140) compared to untreated material. A sample of PVC coated with the polymer showed a reduction in protein adsorption of 60% compared to untreated material as determined by the same assay technique.

EXAMPLE 11

Preparation of poly(2(acryloyloxyethyl)-2' (trimethylammonium)ethyl phosphate inner salt -co- n-dodecyl methacrylate)(1:2)

The polymer was prepared by a method analogous to that described in Examples 4 and 6 using 2(acryloyloxyethyl)- 2'(trimethylammonium)ethyl phosphate inner salt (3.0 g, 0.0107 mole) and n-dodecyl methacrylate (5.42 g, 0.0214 mole) dissolved in propan-2-ol (53 ml) and ethyl acetate (22 ml).

The resulting polymer, obtained in 58% yield was a white solid.

NMR(100 MHz,d,ppm,CD$_3$OD/CDCl$_3$) 4.2–4.4(b), 3.8–4.2(b),3.6–3.8(b),3.3(s),1.8–2.2(b),1.5–1.8(b),1.2–1.5 (s),0.8–1.0(s)

IR(CM$^{-1}$,KBr disc) 3430, 2929, 2854, 1732, 1469, 1246, 1156, 1089, 968, 788.

| Elemental Analysis | | | | |
|---|---|---|---|---|
| theory | C 64.9 | H 8.7 | N 1.8 | P 4.0 |
| actual | C 57.8 | H 9.8 | N 2.1 | P 4.9 |

A sample of stainless steel treated with the polymer showed a reduction in protein adsorption of 53% (determined by the enzyme immunoassay described above) and a reduction in platelet activation of 100% (determined by the platelet activation assay described above, using anti-GMP140) compared to untreated material. A sample of PVC treated with the polymer showed a reduction in protein adsorption of 68% and a reduction in platelet activation of 100% compared to untreated material determined by the same assay techniques.

EXAMPLE 12

Preparation of poly(2(methacryloyloxyethyl)- 2' (trimethylammonium)ethyl phosphate inner salt -co- n-hexyl methacrylate ((1:2)

The polymer was prepared by a method analogous to that described in Examples 4 and 6 using 2(methacryloyloxyethyl)-2'(trimethylammonium)ethyl phosphate inner salt(2.0 g, 0.0068 mole) and n-hexyl methacrylate (2.31 g, 0.0136 mole) dissolved in propan-2-ol (35.5 ml) and ethyl acetate (14.5 ml).

The resulting polymer, obtained in 34% yield was a white solid.

NMR(100 MHz,d,ppm,CD$_3$OD/CDCl$_3$)4.2–4.4(b), 3.8–4.2(b),3.6–3.8(b),3.3(s),1.8–2.2(b),1.5–1.8(b),1.2–1.5 (s),0.8–1.0(s)

IR(cm$^{-1}$,KBr disc) 3430, 2929, 2854, 1732, 1469, 1246, 1156, 1089, 968, 788.

| Elemental Analysis | | | | |
|---|---|---|---|---|
| theory | C 58.8 | H 8.8 | N 2.2 | P 4.9 |
| actual | C 47.3 | H 7.9 | N 2.6 | P 5.8 |

EXAMPLE 13

Preparation of poly(2(methacryloyloxvethyl)-2' (trimethylammonium)ethyl phosphate inner salt -co- n-octadecyl methacrylate) (1:2)

The polymer was prepared by a method analogous to that described in Example 5 using 2(methacryloyloxyethyl)-2' (trimethylammonium)ethyl phosphate inner salt(3.0 g,0.0102 mole) and n-octadecyl methacrylate (6.90 g,0.0204 mole) dissolved in methanol (30 ml) and THF (70 ml). The reaction mixture rate was maintained for 40 hours at 60° C. The polymer was isolated from this mixture by precipitation in acetone (1200 ml), vacuum filtration and drying. The resulting polymer, obtained in 55% yield was a white solid.

NMR(100 MHz,d,ppm,CD$_3$OD/CDCl$_3$)4.2–4.4 (b), 3.8–4.2 (b) ,3.6–3.8(b),3.3(s),1.8–2.2(b),1.5–1.8(b),1.2–1.5 (s),0.8–1.0(s)

IR(cm$^{-1}$,KBr disc) 3430, 2929, 2854, 1732, 1469, 1246, 1156, 1089, 968, 788.

EXAMPLE 14

Preparation of poly(2 (methacryloyloxyethyl)-2' (trimethylammonium)ethyl phospate inne salt -co- n-dodecyl methacrylate -co- 2 hydroxvethvlmethacrylate) (17:75:8)

The polymer was prepared by a method analogous to Examples 4 and 6, using 2(methacryloyloxyethyl)-2' (trimethylammonium)ethyl phosphate inner salt (2.0 g,0.0068 mole), n-dodecyl methacrylate (7.65 g, 0.0301 mole) and 2-hydroxyethyl methacrylate (0.42 g, 0.0032 mole) dissolved in propan-2-ol(70 ml) and ethyl acetate (30 ml).

The resulting polymer, obtained in 53% yield was a white solid.

NMR(100 MHz,d,ppm,CD$_3$OD/CDCl$_3$)4.2–4.4(b) 3.8–4.2(b),3.6–3.8(b),3.3(s),1.8–2.2(b),1.5–1.8(b),1.2–1.5 (s),0.8–1.0(s).

IR(cm$^{-1}$,KBr disc) 3435, 2925, 2860, 1729, 1468, 1243, 1152, 1089, 969, 791.

A coating solution of poly(2(methacryloyloxyethyl)-2' (trimethylammonium)ethyl phospate inner salt -co- n-dodecyl methacrylate -co- 2-hydroxyethylmetacrylate) (0.5097 g) in propan-2-ol (50 ml) was prepared. Aluminium sheet was washed with propan-2-ol, hexane and water and dried, the coating solution (0.5 ml) was applied to pieces of the aluminium sheet (7.5 cm²) by a spin coating technique using a spin speed of 1200 rpm.

EXAMPLE 15

Preparation of poly(2(methacryloyloxyethyl)-2'(trimethylammonium)ethyl phosphate inner salt -co-Methacrylic acid (7:3)

The polymer was prepared by a method analogous to that of Examples 4 and 6 using 2(methacryloyloxyethyl)-2' (trimethylammonium)ethyl phosphate inner salt (4.44 g,0.0149 mole), and methacrylic acid (0.54 g,0.0063 mole) dissolved in propan-2-ol (25 ml) and water (25 ml). The polymer was isolated by precipitation in acetone (500 ml), redissolved in methanol (50 ml) and isolated by precipitation in diethylether (500 ml).

The resulting polymer, obtained in 30% yield was a white solid.

NMR(100 MHz,d,ppm,$CD_3OD/CDCl_3$)4.2–4.4(b), 3.8–4.2(b),3.6–3.8(b),3.3(s),1.8–2.2(b),1.5–1.8(b),$_1$.2–1.5 (s),0.8–1.0(s)

IR($cm^{-1}$,KBr disc) 3430, 2929, 2854, 1732, 1469, 1246, 1156, 1089, 968, 788.

This polymer was used to treat cellulose film which had been treated with 2-aminoethyl methacrylate as follows:

A section of cellulose dialysis membrane (4×6cm) was taken, and placed into a solution of 2-aminopropylmethacrylate (3.34 g) and ceric ammonium nitrate (0.05 g) in distilled water (20 ml). The solution was deoxygenated with $N_2$ for 10 minutes, then the vessel was sealed, and left at room temperature for 2 hours. The cellulose sample was then removed from the solution, then washed extensively in distilled water for 24 hours.

The presence of amine hydrochloride moieties on the grafted sample was demonstrated by the differential uptake of anionic and cationic dyes (Trypton blue and methylene blue respectively).

Strips of the functionalised cellulose (0.5cm×2cm) were placed in a 10% w/w solution of the polymer in water. The samples were left to stand at room temperature for 1 hour, then washed extensively in distilled water (200 ml) for 2 hours.

Following the aqueous wash, the treated cellulose was placed into a solution of acid molybdate spray reagent and left to stand for 1 hour, then removed and washed with distilled water. The presence of phosphate groups on the sample was demonstrated by the development of a blue colour.

EXAMPLE 16

Preparation of poly(2(methacryloyloxvethyl)-2'(trimethylammonium)ethyl phosphate inner salt -co-(2-methacryoyloxyethyl trimethylammonium chloride (7:3)

2(Methacryloyloxyethyl)-2'(trimethylammonium)ethyl phosphate inner salt (4.45 g,0.0151 mole), 2-methacryoyloxyethyl trimethylammonium chloride(1.96 g of a 75% aqueous solution, 0.0071 mole) were dissolved in ethanol (50 ml). The solution was stirred (250 rpm) at 23° C. under a stream of nitrogen (50 ml/min) for 30 minutes. 2,2'-Azo-bis(2-methylpropionitrile) (0.02 g,0.122 mole) was added and the flow of nitrogen was reduced to 10 ml/min, the reation temperature as raised to 60° C. This temperature and nitrogen flow rate ere maintained for 40 hours.

The mixture was allowed to cool and filtered under vacuum. The polymer was isolated from this mixture by precipitation in diethylether (500 ml), vacuum filtration and drying.

The resulting polymer, obtained in 68% yield was a white solid.

NMR(100 MHz,d,ppm,$CD_3OD/CDCl_3$) 4.2–4.4(b) ,3.8–4.2(b) ,3.6–3.8(b) ,3.3(s),1.8–2.2(b),1.5–1.8(b),1.2–1.5 (s),0.8–1.0(s)

IR($cm^{-1}$,KBr disc) 3430, 2929, 2854, 1732, 1469, 1246, 1156, 1089, 968, 788.

The polymer was used to treat cellulose film which had been treated with 3-sulfopropyl methacrylate potassium salt using the method described in Example 15 but using 3-sulfopropyl methacrylate potassium salt (4.92 g) rather than 2-aminopropyl methacrylate.

The presence of sulphate moieties on the grafted sample was demonstrated by the differntial uptake of anionic and cationic dyes (Trypton blue and methylene blue respctively).

Strips of the functionalised cellulose (0.5cm×2cm) were treated with a lot w/w solution of the polymer in water in an analogous manner to that described in Example 15 and the presence of phosphate groups was demonstrated in the same way.

EXAMPLE 17

Preparation of poly(2(methacryloyloxyethyl)-2'(trimethylammonium)ethyl phosphate inner salt -co-n-dodecyl methacrylate (14:86)

The polymer was prepared by a method analogous to that described in Example 1 using a comonomer mixture consisting of 2 (methacryloyloxyethyl) -2' (trimethylammonium) ethyl phosphate inner salt and n-dodecyl methacrylate in a molar ratio of 14:86 using propan-2-ol/ethylacetate solvent.

A PVC substrate was coated with the polymer using a method analogous to that described in Example 3.

Comparative Example

The fibrinogen adsorption and C-reactive protein binding to PVC substrates coated with polymers of the invention in accordance with Examples 3 and 17 was compared with that for copolymers of 2(methacryloyloxyethyl)-2'(trimethylammonium)ethyl phosphate, inner salt and butyl methacrylate in a molar ratio of 1:2 (Comparison A) and 14:86 (Comparison B). The comparison copolymers were prepared by a method analogous to that described in Example 1 and coated onto the PVC substrate using a method analogous to that described in Example 3. All the copolymers were prepared using the procedure described under Example 1 using a propan-2-ol/ethylacetate solvent. The results are shown in the following Table:

|  | Example | | Comparison | |
| --- | --- | --- | --- | --- |
|  | 3 | 17 | A | B |
| Fibrinogen Adsorption | 87 | 60 | 82 | 72 |
| C-reative Protein | 0.094 | 0.043 | 0.101 | 0.139 |
| Protein Index (×10³) | 1.1 | 0.7 | 1.9 | 1.9 |

The results were obtained using the assay techniques described above after incubation in PBS for 24 hours. The fibrinogen adsorption results are expressed as a percentage reduction in optical density relative to untreated Polyvinylidene chloride. C-reactive protein results are expressed as absorbance due to C-reactive protein; a positive control showed CRP binding. Protein index is the ratio of C-reactive protein binding to fibrinogen adsorption.

These results show that in order to obtain a good reduction in protein adsorption using copolymers containing butylmethacrylate a high C-reactive protein binding must be accepted. In contrast, using longer chain alkyl monomers good reduction in protein adsorption and low C-reactive protein binding are obtained as well as good adhesion to the substrate and low swelling in aqueous environments.

Copolymers containing comonomers comprising short chain alkyl groups of up to 4 carbon atoms as potential physisorbable groups such as butyl methacrylate, in smaller molar proportions, exhibit poor adhesion to hydrophobic substrates and are subject to high swelling in aqueous environments which renders them unsuitable for use in coating surfaces.

EXAMPLE 18

Polymers from examples 1 and 4 were coated onto PVC tubing and their performance assessed in an extracorporeal system using a left heart bypass procedure in a calf model. Blood was pumped around the system continuously at physiological temperature in the absence of anticoagulant at a rate of 3.5 litre per minute. Parameters associated with the condition of circulating blood were measured throughout the experiments.

Virtually all the parameters tested gave results which showed that the presence of the coated circuit had little or no effect on the blood and the physiological function of the animals (typically three identical experiments were run on consecutive days and were very reproducible from animal to animal).

In comparison with the above an uncoated circuit cannot be successfully run for a continuous 6 hour period without the use of anticoagulant. Also blood parameters are very adversely affected in a short period of time.

Results of protein adsorption tests and macroscopic observation of circuit components indicate that both coatings perform at least as well as heparinised tubing and that, in areas of the circuit where high turbulence in the flow of the blood occurs, fewer clots were found.

Reference Example 1

Preparation of 2(methacryloyloxyethyl)-2'(trimethylammonium ethyl phosphate inner salt The preparation is illustrated by the reaction scheme A which follows.
a) 2-Chloro-1,3-dioxaphospholane (1)

In a flask fitted with a pressure equalising dropping funnel, reflux condenser (fitted with a $CaCl_2$ guard tube) and magnetic stirrer, was placed a solution of phosphorus trichloride (220 ml; 346.3 g; 2.52 mol) in dichloromethane (500 ml). Ethylene glycol (139 ml; 154.7 g, 2.49 mol) was then added dropwise via the dropping funnel at such a rate that the evolution of HCl did not become too excessive. On the addition of the ethylene glycol, the condenser was arranged for distillation, and the dichloromethane removed at atmospheric pressure. When the distillate temperature reached 60° C. the flask was arranged for vacuum distillation using a water pump. Distillation then gave 2-chloro-1,3-dioxaphospholane (158 ml; 224.5 g; 71.3%) as a colourless mobile liquid (which fumes in moist air) b.pt. 36°–40° C./21 mm Hg. [cf 45.5°–47° C./20 mm Hg, Lucas et al. J. Am. Chem. Soc., 72, 5491, (1950)].

IR (cm$^{-1}$, thin film) 2980, 2905, 1470, 1210, 1005, 930, 813, 770.

b) 2-Chloro-2-oxo-1,3,2-dioxaphospholane (2)

In a flask fitted with a magnetic stirrer, reflux condenser (fitted with a $CaCl_2$ guard tube) and sintered glass gas inlet tube, was placed a solution of 2-chloro-1,3-2-dioxaphospholane (100.8 g; 0.797 mol) in dry benzene (200 ml). The solution was stirred and a steady stream of oxygen was bubbled through the solution. The reaction was mildly exothermic, and temperature control was achieved by allowing the solvent to reflux. The oxygen was passed through the reaction mixture for 6 hours. The solvent was removed by rotary evaporation, and the colourless mobile residue distilled to give 2-chloro-2-oxo-1,3,2-dioxaphospholane (2) (87.41 g; 77%) as a colourless mobile liquid -b.pt 95°–97° C./0.2 mbar (c.f. 102.5°–105° C./1 mbar (Edmundson, Chem. Ind. (London)), 1828 (1962); 79° C./0.4 mbar [Umeda et al., Makromol. Chem. Rapid Commun., 3, 457, (1982)].

IR(cm$^{-1}$, thin film) 2990, 2910, 1475, 1370, 1310, 1220, 1030, 930, 865, 830.

c) 2(2-Oxo-1,3,2-dioxaphospholan-2-yloxy)ethyl methacrylate (3)

In a flask fitted with a magnetic stirrer, low temperature thermometer, and a pressure equalising funnel fitted with a silica gel guard tube, was placed a solution of 2-hydroxyethylmethacrylate (20. 00 g, 0. 154 mol) and triethylamine (15.60 g; 0.154 mol) in dry diethyl ether (300 ml). The solution was stirred and cooled to between -20° C. and -30° C. A solution of freshly distilled 2-chloro-2-oxo-1,3,2-dioxaphospholane(2) (21.9 g; 0.154 mol) in dry diethyl ether (20 ml) was then added dropwise over 30 minutes, the temperature being held at -20° C. during the addition. Stirring was continued at this temperature for a further 1 hour and then for a further hour as the reaction mixture was allowed to warm to room temperature. The precipitated triethylamine hydrochloride was removed by filtration, and was washed well with dry ether. The ether was removed from the combined filtrate and washings by rotary evaporation. The cloudy oil residue was then shaken for 5 minutes with dry diethyl ether (50 ml) to precipitate a further crop of triethylamine hydrochloride, which was again removed by filtration. Removal of the ether on the rotary evaporator gave (3) (34.18 g; 94.3%) as a colourless viscous oil.

IR (cm$^{-1}$, thin film) 1720, 1640, 1450, 1360, 1310, 1290, 1170, 1030, 930, 850.

NMR (CDCl$_3$; 60MHz, 6 ppm) 1.95 (s,3H), 4.25–4.70 (m,8H), 5.70 (m,1H), 6.25 (m,1H).

Rf 0.9 (SiO$_2$, eluting with 10% methanol:90% dichloromethane; spot visualised with molybdenum blue spray reagent and with iodine vapour).

(d) 2(Methacryloyloxyethyl)-2'(trimethylammonium)ethyl phosphate inner salt (4).

The phospholane (3) (67.20 g; 0.285 mol) was dissolved in 100 ml of dry acetonitrile, and placed in a heavy walled tissue culture bottle. The phospholane solution was then treated with a solution of anhydrous trimethylamine (25.74 g; 0.436 mol) in dry acetonitrile (100 ml). The vessel was then sealed, and placed in a water bath held at 50° C. for 30 hours. The vessel was opened, and the solution brought to the boil. The solution was filtered whilst hot, and then set aside for crystallisation.

The product was collected by filtration, and most of the solvent removed by suction. The wet product was then washed thoroughly with anhydrous ether, then dried under reduced pressure, to give (4) as a white amorphous, hygroscopic solid (51.16 g; 61%). Evaporation of the mother liquor gave a very viscous oil (20.00 g; 23%), from which further product (4) crystallised on standing at −20° C. TLC (silica gel plates, eluting with methanol/dichloromethane (1:1 v/v)) showed one spot Rf 0.1, which was revealed with Dragendorff's reagent, Molybdenum blue spray reagent, and iodine vapour.

IR(cm$^{-1}$ 1720, 1640, 1320, 1300, 1230, 1170, 970, 750. NMR (D$_2$O; 60MHz; δ ppm) 2.0 (s,3H), 3.27 (s,9H) 3.60–4.50 (m, 8H), 5.80, (m,1H) and 6.25 (m,1H). CHN Found: C 42.98%, H 7.88%, N 4.42%, P 10.51%. CHN Theory: C 44.75%, H 7.46%, N 4.75%, P 10.51%.

Reference Example 2:

Synthesis of dimethyl(2-methacroyloxyethyl)-(1(2-sulphopropyl)) ammonium betaine inner salt 2(Dimethylamino)ethylmethacrylate was vacuum distilled and then dissolved in 0.1 M dichloromethane. To this solution was added an equimolar amount of propane sultone. The betaine slowly precipitated out of solution and was recovered by filtration and washed with cold dichloromethane. The reaction is shown in Reaction Scheme B.

Reference Example 3

Preparation of 1[4(4'-vinylbenzyloxy)butane]-2"-(trimethylammonium)ethyl phosphate inner salt.

The synthesis is depicted in Reaction Scheme C.
4-Hydroxy-1(4'-vinylbenzyloxy)butane (5)

Butanediol (40 ml; 40.68 g; 0.452 mol) was stirred in a 100 ml round bottomed flask, and treated portionwise with potassium butoxide (17.60 g; 0.144 mol). The initial reaction was exothermic. The reaction mixture was stirred for 1.5 hours at room temperature. The resulting cloudy solution was then treated with chloromethyl styrene (20.00 g; 0.131 mol). The styrene formed an upper, pale green layer, (the colouration being due to the presence of inhibitor), whose color darkened considerably on the addition of 18-crown-6 (0.49 g; 1.86×10$^{-3}$ mole). The flask was stoppered, protected from light, and stirred for 28 hours at room temperature. The mixture was then poured into water (120 ml) and extracted with dichloromethane (4×50 ml). The combined organic extracts were dried (MgSO$_4$) and evaporated to give viscous yellow oil (932.7 g). This oil was distilled from a small amount of CuCl to give a product showing some impurities on TLC. The oil was then chromatographed on silica gel, initially eluting with dichloromethane/petrol (1:1) to remove the impurities. The product was then eluted off the column with ethyl acetate/petrol (1:1). Evaporation of the solvent gave a colourless oil, which was distilled to give the desired styrylbutyl alcohol as a colourless oil b.pt. 150°–152°/0.4mbar. Yield 18.70 g; 69.2%.

NMR (60MHz: CDCl$_3$) 1.55 (m,4H C—CH$_2$—C) ; 3.50 (m, 5H, 1H exch.; O—CH$_2$—, O—H), 4.45 (s,2H; Ar—CH$_2$—), 5.50 (dd, 2H, vinylic), 6.75 (dd, vinylic), 7.40 (m, 4H, Ar—H).

IR 3402, 2938, 2888, 1631, 1602, 1582, 1511, 1480, 1445, 1382, 1320, 1116, 1063, 920, 907, 827, 801, 716 and 667 cm$^{-1}$ 4(2-Oxo-1,2,3-dioxaphospholane-2-yloxvl-1(4'-vinylbenzyloxy)butane (6)

4-Hydroxy-1(4'-vinylbenzyloxy)butane (5) (10.03 g; 48.69 mmol) and dried triethylamine (4.92 g, 48.69 mmol) were dissolved in dry diethyl ether (150 ml) and the resulting solution placed in a rigorously dried flask. The solution was cooled to −30° C. and 2-chloro-2-oxo-1,3,2-dioxaphospholane (6.94 g; 48.69 mmol) added dropwise over 30 minutes, the temperature being held at −30° C. The reaction mixture was then stirred for a further 2 hours, during which time the temperature was allowed to rise to 10° C. The mixture was filtered and the precipitate washed with dry ether. The filtrate was evaporated (20° C./21mm) to give a cloudy oil. The residue was shaken with 50 ml of dry ether and refiltered. Evaporation of the filtrate gave the product as a viscous yellow oil (13.73 g; 90.4%).

TLC (eluting with 10% methanol 90% dichloromethane) showed one major spot, which stained with acid molybdate reagent (Rf 0.61), IR (thin film) 3458, 2945, 2917, 2860, 1630, 1602, 1581, 1475, 1419, 1363, 1283, 1103, 1032, 820, 842, 807, 800, 715, 610 and 421 cm$^{-1}$.

1[4(4'-Vinylbenzyloxy)butane]-2"(trimethylammonium) ethyl phosphate inner salt (7)

Trimethylamine (2.00 g, 33.9 mmol) was distilled into a reaction vessel, and frozen with liquid nitrogen. A solution of the 4(2-oxo-1,3,2-dioxaphospholane-2-yloxy)-1-(4'-vinylbenzyloxy)butane (6) (10.00 g, 32.1 mmol) in anhydrous acetonitrile (40 ml) was then added to the reaction vessel, which was then sealed and placed in a thermostatted water bath (50° C. for 50 hours). The reaction vessel was then cooled to room temperature, opened, and the reaction mixture evaporated to about half its original volume (21 mm pressure). The concentrated solution was then stirred at room temperature, whilst anhydrous ether (200 ml) was added dropwise to precipitate the product as a viscous oil. The mixture was then left for several hours at −10° C. The product was collected by decanting off the supernatent solid. TLC (eluting with methanol/dichloromethane 1:1) showed one major spot at Rf 0.0–0.1 which stained with both Dragendorffs reagent and acid molybdate.

Reference Example 4

Preparation of 2(acryloyloxyethyl)-2'-(trimethylammonium)ethyl phosphate inner salt The synthesis is essentially analogous to that described in Reference Example 1 and uses a synthetic strategy analogous to that shown in Reaction Scheme A.

(a) 2-(2-Oxo-1,3,2-dioxaphospholan-2-yloxy)ethyl acrylate

2-Hydroxyethyl acrylate (11.5 ml, 0.1 M) and triethylamine (14.6 ml) in dry diethyl ether (250 ml) were cooled to −25° C. under nitrogen as a solution of 2-chloro-2-oxo-1,3,2-dioxaphospholane (14.3 g) in dry diethyl ether was added over 20 minutes. The mixture was stirred for a further 1 hour at −20° C. and then allowed to warm to 10° C. over a further hour. The precipitate was filtered, washed with ethyl acetate (100 ml) and the combined filtrate and washings evaporated under reduced pressue to give a pale yellow oil (21 g).

$^1$H NMR (200MHz) d (CD$_3$CN) 6.4 (1H,dd), 6.2 (1H,dd), 5.9 (1H,dd), 4.0–3.6 (8H,complex) ppm.

(b) 2-(Acryloyloxyethyl)-2'-(trimethylammonium)ethyl phoshate, inner salt.

2-(2-Oxol,3,2-dioxaphospholan-2yloxy) ethyl acrylate (21 g,0.095M) in acetonitile (50 ml) was treated with a solution of triethylamine (12.1 g) in acetonitrile (150 ml) in a pressure reactor at 50° C. for 17 hours. The mixture was cooled and some of the excess triethylamine removed by evaporation under reduced pressure.

The solid material was filtered under nitrogen, washed with acetonitrile (20 ml) and diethylether (50 ml) and then dried under reduced pressue to give a colourless oil (12.1 g, 45%).

$^1$H NMR (200MHz) d (D$_2$O) 6.45 (1H,dd,J1.2 and 17.1 Hz), 6.25 (1H,dd,J1.2 and 10.25Hz), 6.02 (1H,dd, J1.23 and 10.25Hz), 4.4 (2H,m), 4.3 (2H, m), 4.2 (2H,m) 3.6(2H,m) and 3.2(9H,s) ppm.

Reference Example 5

Dodec-7-yn-1-ol Methacrylate

To dodec-7-yn-1-ol (25 g) in dichloromethane (60 ml) was added distilled triethylamine (14.1 g). The mixture was cooled in an ice bath (0.5° C.) and stirred as distilled methacryloyl chloride (16.2 g) in dichloromethane (50 ml) was added over 10 minutes. The temperature of the reation was allowed to warm to ambient and the mixture stirred for two hours. Water (150 ml) was added and the organic layer was removed and successively extracted with water (2×150 ml) and saturated sodium bicarbonate solution (2×150 ml), washed with brine (150 ml) and dried over anhydrous sodium sulphate. The solvent was removed under reduced pressure to give a pale yellow oily liquid which was distilled under reduced pressure (0.18 mBar, 106°–110° C.) in the presence of copper (1) chloride to give dodec-7-yn-1-ol methacrylate, 17 g, 50% yield.

$^1$H-NMR (200 MHz,d,ppm,CDCl$_3$): 0.90 (t,3H), 1.45 (m,10H), 1.70 (m,2H), 1.95 (s,3H), 2.15 (m,6H), 4.15 (t,2H), 5.55 (s,1H), 6.10 (s,1H).

Reaction Scheme A

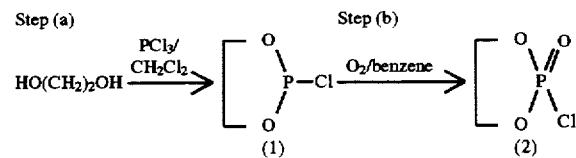

-continued
Reaction Scheme A

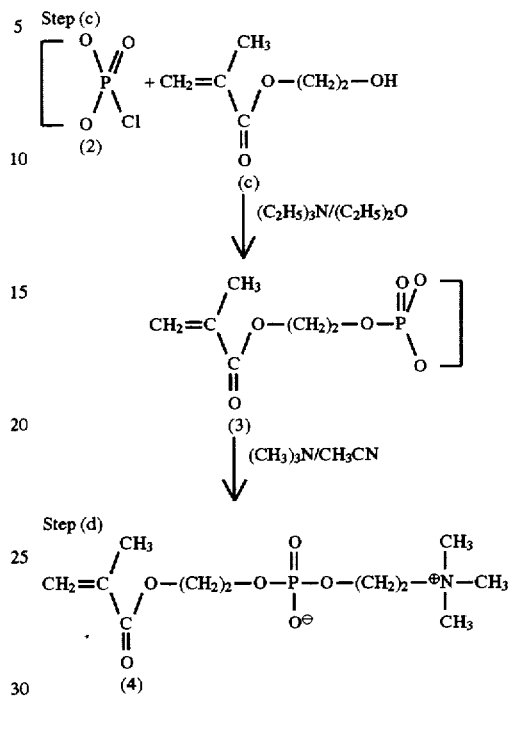

Steps (a) to (d) correspond with the steps in Reference Example 1

Reaction Scheme B

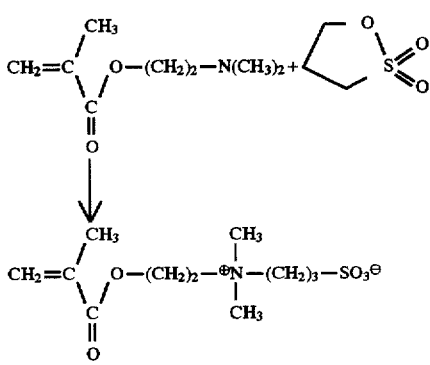

Reaction Scheme C

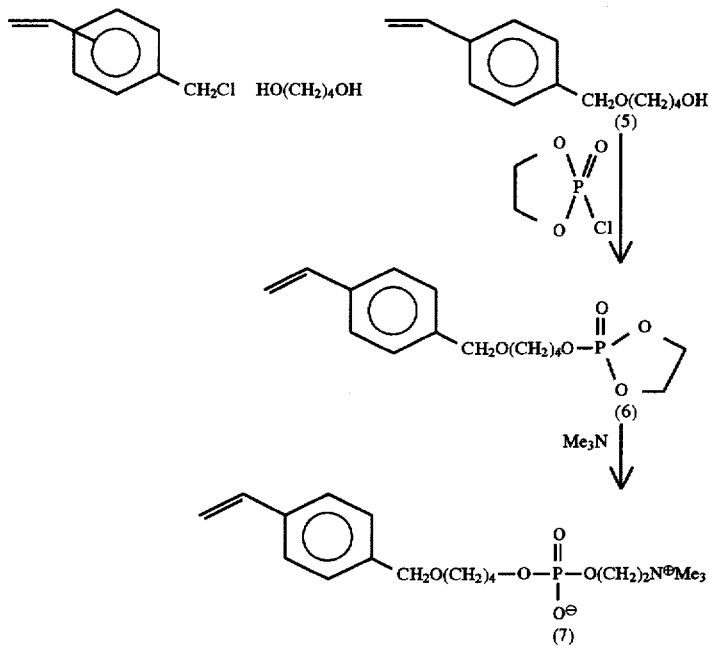

We claim:

1. A biocompatible polymer formed from monomers consisting of: (A) a radical polymerizable zwitterionic monomer containing a zwitterionic group, (B) a radical polymerizable ionic comonomer containing an ionic group, and, optionally, (C) a radically polymerisable diluent monomer, wherein the monomer A is a compound of formula Y—B—X, wherein X is a zwitterionic group;

B is a straight or branched alkylene, oxaalkylene, oligooxaalkylene chain optionally containing one or more fluorine atoms up to and including perfluorinated chains, or if X contains a carbon-carbon chain between B and the zwitterion or if Y contains a terminal carbon atom bonded to B, a valence bond;

Y is an ethylenically unsaturated polymerizable group selected from

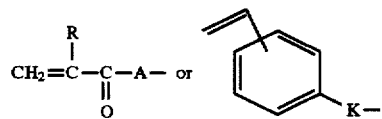

wherein:

R is hydrogen or a $C_{1-4}$ alkyl group;

A is —O— or —$NR^1$— where $R^1$ is hydrogen or a $C_{1-4}$ alkyl group or $R^1$ is —B—X where B and X are as defined above; and K is selected from the group consisting of —$(CH_2)_pOC(O)$—, —$(CH_2)_pC(O)O$—, —$(CH_2)_pOC(O)O$—, —$(CH_2)_pNR2$—, —$(CH_2)_pNR^2C(O)$—, $(CH_2)_pC(O)NR^2$—, —$(CH_2)_pNR^2C(O)O$—, —$(CH_2)pOC(O)NR^2$—, —$(CH_2)_pNR^2C(O)NR^2$— (in which $R^2$ may be the same or different), —$(CH_2)_pO$—, —$(CH_2)_pSO_3$—, and, optionally in combination with B, a valence bond and p is from 1 to 12 and $R^2$ is hydrogen or a $C_{1-4}$ alkyl group;

wherein the comonomer (B) is a compound of formula $Y^2$—$B^9$—$Q^5$;

where $Y^2$ is an ethylenically unsaturated polymerizable group selected from

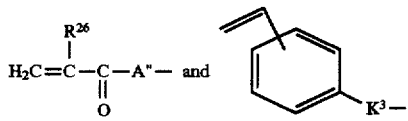

where $R^{26}$ is hydrogen or $C_{1-4}$ alkyl;

A" is —O— or $NR^{27}$—, wherein $R^{27}$ is hydrogen or a $C_{1-4}$ alkyl group or $R^{27}$ is —$B^9Q^5$, $B^9$ is a valence bond, a straight or branched alkylene oxaalkylene or oligo-oxaalkylene group;

$K^3$ is —$(CH_2)_xOC(O)$—, —$(CH)_xC(O))$—, $(CH_2)_xOC(O)$—, —$(CH_2)_xNR^{28}$—, —$(CH_2)_xNR^{28}C(O)$—, —$(CH_2)_xC(O)NR^{28}$—, —$(CH_2)_xNR^{28}C(O)O$—, —$(CH_2)_xNR^{28}$—, —$(CH_2)_xNR^{28}C(O)NR^{28}$— (in which the $R^{28}$ groups are the same or different), —$(CH_2)_xO$—, —$(CH_2)_xSO_3$—, a valence bond, x is from 1 to 12 and $R^{28}$ is hydrogen or a $C_{1-4}$ alkyl group; and $Q^5$ is an ionic group, and wherein the diluent monomer (C) is a monomer not having said zwitterionic group or said ionic group, and is selected from the group consisting of an alkyl(alk) acrylate; an alkyl (alk) acrylamide: a hydroxyalkyl (alk)acrylate: vinyl pyrrolidone; styrene; a polyhydroxyl (alk)acrylate and a polyhydroxyl (alk) acrylamide in which the alkyl group contains from 1 to 4 carbon atoms; a polymerisable $C_{2-4}$ alkene; a polymerisable butadiene; and a polymerisable acrylonitrile.

2. A polymer according to claim 1 formed from a monomer containing both said zwitterionic group and said pendant ionic group.

3. A polymer according to claim 1 in which the group $Q^5$ is selected from the group consisting of carboxylate; sulphonate; hydrogen phosphate; phosphate; groups $-NR^{31}{}_3{}^+$ in which each group $R^{31}$ is the same or different, and is hydrogen or alkyl of 1 to 6 carbon atoms two of which groups $R^{31}$ may together form a heterocyclic ring containing from 5 to 7 atoms, groups $N^+$Het, where Het is an unsaturated heterocyclic group substituted or unsubstituted by one or more alkyl groups of 1 to 4 carbon atoms; and groups $-PR^{32}{}_3{}^+$ in which each group $R^{32}$ is the same or different and is hydrogen or alkyl of 1 to 6 carbon atoms, two of which groups $R^{31}$ may together form a heterocyclic ring containing 5 to 7 atoms.

4. A polymer according to claim 3 in which the group $Q^5$ is selected from the group consisting of carboxylate, sulphonate, phosphate and groups $-NR^{31}{}_3{}^+$ in which each group $R^{31}$ is the same or different and is hydrogen or methyl.

5. A polymer according to claim 1 in which X is selected from groups IVB, IVC, IVD, and IVF in which IVB has the formula

wherein the groups $R^6$ are the same or different and each is hydrogen or $C_{1-4}$ alkyl and d is from 2 to 4;

group IVC has the formula

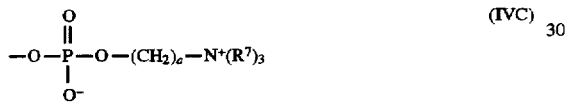

wherein the groups $R^7$ are the same or different and each is hydrogen or $C_{1-4}$ alkyl, and e is from 1 to 4;

group IVD has the formula

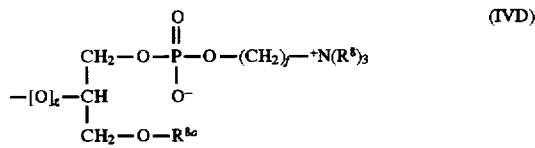

wherein the groups $R^8$ are the same or different and each is hydrogen or $C_{1-4}$ alkyl, $R^{8a}$ is hydrogen or a group $-C(O)B^1R^{8b}$ wherein $R^{8b}$ is hydrogen or methyl, $B^1$ is a valence bond or straight or branched alkylene, oxaalkylene or oligo-oxaalkyene group, and f is from 1 to 4; and if B is other than a valence bond z is 1 and if B is a valence bond z is 0, if X is directly bonded to an oxygen or nitrogen atom and otherwise z is 1;

group IVE has the formula

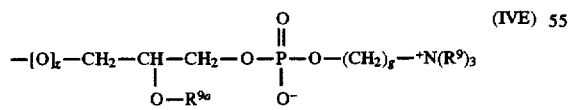

wherein the groups $R^9$ are the same or different and each is hydrogen or $C_{1-4}$ alkyl, $R^{9a}$ is hydrogen or a group $-C(O)B^2R^{9b}$, wherein $R^{9b}$ is hydrogen or methyl, $B^2$ is a valence bond or a straight or branched alkylene, oxaalkylene or oligo-oxaalkylene group, and g is from 1 to 4; and if B is other than a valence bond is 1 and if B is a valence bond z is 0 if X is directly bonded to an oxygen or nitrogen atom and otherwise z is 1; and group IVF has the formula

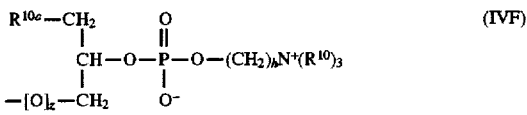

wherein the groups $R^{10}$ are the same or different and each is hydrogen or $C_{1-4}$ alkyl, $R^{10a}$ is hydrogen or a group $-C(O)B^3R^{10b}$ wherein $R^{10b}$ is hydrogen or methyl, $B^3$ is a valence bond or a straight or branched alkylene, oxaalkylene or oligo-oxaalkylene group, and h is from 1 to 4;

if B is other than a valence bond z is 1 and if B is a valence bond z is 0 if X is directly bonded to the oxygen or nitrogen and otherwise z is 1.

6. A polymer according to claim 1 in which the ratio of zwitterionic monomer to ionic comonomer is in the range 5:95 to 95:5.

7. A polymer according to claim 1 formed from monomers including 5 to 50% by mole of diluent monomer not having said zwitterionic group or said ionic group.

8. A polymer-forming process comprising the step of forming a biocompatible polymer by radical polymerization of (A) a zwitterionic monomer containing a zwitterionic group and (B) a comonomer containing an ionic group, wherein the monomer A is a compound of formula Y—B—X.

wherein B is a straight or branched alkylene, oxaalkylene, oligooxaalkylene chain optionally containing one or more fluorine atoms up to and including perfluorinated chains, or if X contains a carbon-carbon chain between B and the center of permanent position charge or if Y contains a terminal carbon atom bonded to B, a valence bond;

X is a zwitterionic group, and

Y is an ethylenically unsaturated polymerizable group selected from

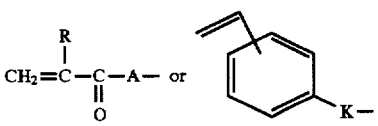

wherein:

R is hydrogen or a $C_{1-4}$ alkyl group;

A is —O— or —NR$^1$— where $R^1$ is hydrogen or a $C_{1-4}$ alkyl group or $R^1$ is —B—X where B and X are as defined above; and K is selected from the group consisting of —$(CH_2)_p$OC(O)—, —$(CH_2)_p$C(O)O—, —$(CH_2)_p$OC(O)O—, $(CH_2)_p$NR$^2$—, —$(CH_2)_p$NR$^2$C(O)—, $(CH_2)_p$C(O)NR$^2$—, —$(CH_2)_p$NR$^2$C(O)O—, —$(CH_2)$OC(O)NR$^2$—, —$(CH_2)_p$NR$^2$C(O)NR$^2$— (in which $R^2$ may be the same or different), —$(CH_2)_p$O—, —$(CH_2)_p$SO$_3$—, and, optionally in combination with B, a valence bond and p is from 1 to 12 and $R^2$ is hydrogen or a $C_{1-4}$ alkyl group;

and wherein the comonomer B is a compound of formula $Y^2$—$B^9$—$Q^5$;

where $Y^2$ is an ethylenically unsaturated polymerizable group selected from

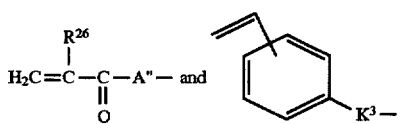

where $R^{26}$ is hydrogen or $C_{1-4}$ alkyl;

A" is —O— or $NR^{27}$—, wherein $R^{27}$ is hydrogen or a $C_{1-4}$ alkyl group or $R^{27}$ is —$B^9Q^5$, $B^9$ is a valence bond, a straight or branched alkylene oxaalkylene or oligo-oxaalkylene group;

$K^3$ is —$(CH_2)_xOC(O)$—, —$(CH)_xC(O))$—, $(CH_2)_xOC(O)$—, —$(CH_2)_xNR^{28}$—, —$(CH_2)_xNR^{28}C(O)$—, —$(CH_2)_xC(O)NR^{28}$—, —$(CH_2)_xNR^{28}C(O)O$—, —$(CH_2)_xOC(O)NR^{28}$—, —$(CH_2)_xNR^{28}C(O)NR^{28}$— (in which the $R^{28}$ groups are the same or different), —$(CH_2)_xO$—, —$(CH_2)_xSO_3$—, a valence bond, x is from 1 to 12 and $R^{28}$ is hydrogen or a $C_{1-4}$ alkyl group; and $Q^5$ is an ionic group.

9. A polymer according to claim 4 in which X is selected from groups IVB, IVC, IVD, IVE, and IVF, in which IVB has the formula

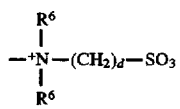

(IVB)

wherein the groups $R^6$ are the same or different and each is hydrogen or $C_{1-4}$ alkyl and d is from 2 to 4;

group IVC has the formula

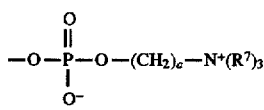

(IVC)

wherein the groups $R^7$ are the same or different and each is hydrogen or $C_{1-4}$ alkyl, and e is from 1 to 4;

group IVD has the formula

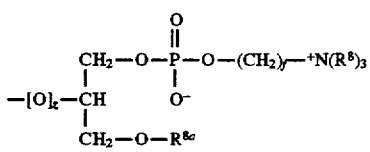

(IVD)

wherein the groups $R^8$ are the same or different and each is hydrogen or $C_{1-4}$ alkyl, $R^{8a}$ is hydrogen or a group —C(O)$B^1R^{8b}$ wherein $R^{8b}$ is hydrogen or methyl, $B^1$ is a valence bond or straight or branched alkylene, oxaalkylene or oligo-oxaalkyene group, and f is from 1 to 4; and if B is other than a valence bond z is 1 and if B is a valence bond z is 0, if X is directly bonded to an oxygen or nitrogen atom and otherwise z is 1;

group IVE has the formula

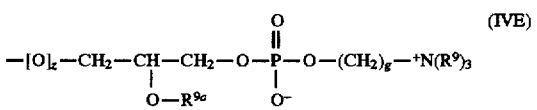

(IVE)

wherein the groups $R^9$ are the same or different and each is hydrogen or $C_{1-4}$ alkyl, $R^{9a}$ is hydrogen or a group —C(O)$B^2R^{9b}$, wherein $R^{9b}$ is hydrogen or methyl, $B^2$ is a valence bond or a straight or branched alkylene, oxaalkylene or oligo-oxaalkylene group, and g is from 1 to 4; and if B is other than a valence bond is 1 and if B is a valence bond z is 0 if X is directly bonded to an oxygen or nitrogen atom and otherwise z is 1; and group IVF has the formula

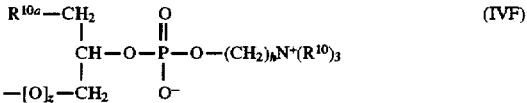

(IVF)

wherein the groups $R^{10}$ are the same or different and each is hydrogen or $C_{1-4}$ alkyl, $R^{10a}$ is hydrogen or a group —C(O)$B^3R^{10b}$ wherein $R^{10b}$ is hydrogen or methyl, $B^3$ is a valence bond or a straight or branched alkylene, oxaalkylene or oligo-oxaalkylene group, and h is from 1 to 4;

if B is other than a valence bond z is 1 and if B is a valence bond z is 0 if X is directly bonded to the oxygen or nitrogen and otherwise z is 1.

10. A polymer according to claim 1 in which the comonomer containing an ionic group is a compound of formula $CH_2$=C ($R^{26}$)—C (O)—A"—$B^9$—$Q^5$, where $R^{26}$ is hydrogen or methyl;

A" is —O—;

$B^9$ is an alkylene group of formula —$(CH_2)_y$—, in which y is 1 to 12 or $B^9$ is a bond; and $Q^5$ is an ionic group selected from a carboxylate group, a sulphonate group, a hydrogen phosphonate group, a phosphate group, a hydroxyl group and groups +$NR^{21}_3$ in which each group $R^{31}$ is the same or different and is hydrogen or methyl, provided that $Q^5$ can be hydroxyl only when $B^9$ is a bond.

11. A polymer according to claim 1 in which the monomer containing a zwitterionic group is a compound of formula $CH_2$=C(R)—C(O)—A—B—X wherein R is hydrogen or methyl;

A is —O—;

B is an alkylene group of formula —$(CH_2)_a$—, wherein a is from 1 to 12; and

X is a group of formula IVC

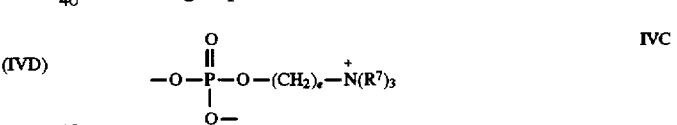

IVC wherein the groups $R^7$ are the same or different and each is hydrogen or $C_{1-4}$-alkyl; and e is from 1 to 4.

12. A polymer according to claim 10 in which the monomer containing a zwitterionic group is a compound of the general formula $CH_2$=C(R)—C(O)—A—B—X wherein R is hydrogen or methyl;

A is —O—;

B is an alkylene group of formula —$(CH_2)_a$—, wherein a is from 1 to 12; and

X is a group of formula IVC

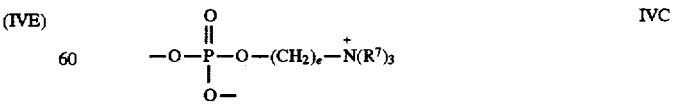

IVC wherein the groups $R^7$ are the same or different and each is hydrogen or $C_{1-4}$-alkyl; and e is from 1 to 4.

* * * * *

UNITED STATES PATENT AND TRADEMARK OFFICE
CERTIFICATE OF CORRECTION

PATENT NO. : 5,783,650
DATED : July 21, 1998
INVENTOR(S) : RODERICK W.J. BOWERS, STEPHEN A. JONES, PETER W. STRATFORD AND STEPENS A. CHARLES It is certified that error appears in the above-identified patent and that said Letters Patent is hereby corrected as shown below:

In Column 7, line 40, change "fluroalkyl" to --fluoroalkyl--.
In Column 7, line 59, change "physiosorption" to --physisorption--.
In Column 8, lines 16 and 19, change "Z" to --$Z^{\ominus}$--.
In Column 9, lines 15, 16, 17, 60, 61 and 62, change "Z" to --z--.
In Column 9, line 34, change "-($CR_{4a2}$)-" to -- -($CR^{4a}_2$)- --.
In Column 10, lines 36, 37 and 38, change "Z" to --z--.
In Column 11, lines 34, 35 and 36, change "Z" to --z--.
In Column 11, line 54, change "$R^{2d}$" to --$R^{3d}$--.
In Column 12, lines 59, 60 and 61, change "Z" to --z--.
In Column 13, lines 9, 10, 11 and 12 (in formula), change "$R^{3c}$" to --$R^{3e}$--.
In Column 13, line 19 (in formula), change "$(CR^{4c}_2)_{bc}$" to --$[(CR^{4e}_2)_{be}O]_{ce}$--.
In Column 13, lines 19, 20, 21, 22, 27, 45 and 47, change "$R^{4c}$" to --$R^{4e}$--.
In Column 13, lines 26 and 45 (in formula), change "$[CR^{4c}_2)_{bc}O]_{cc}$" to --$[(CR^{4e}_2)_{be}O]_{ce}$--.
In Column 14, lines 14, 15 and 16, change "Z" to --z--.
In Column 14, line 42, change "-($CRf_2$)-" to -- -($CR^{4f}_2$)- --.
In Column 15, line 10, change "-$B^6$-$RI^{13a}$" to -- -$B^6$-$R^{13a}$--.

UNITED STATES PATENT AND TRADEMARK OFFICE
CERTIFICATE OF CORRECTION

PATENT NO. : 5,783,650
DATED : July 21, 1998
INVENTOR(S) : RODERICK W.J. BOWERS, STEPHEN A. JONES, PETER W. STRATFORD AND STEPENS A. CHARLES It is certified that error appears in the above-identified patent and that said Letters Patent is hereby corrected as shown below:

In Column 16, line 15 to 28 (in diagram), change

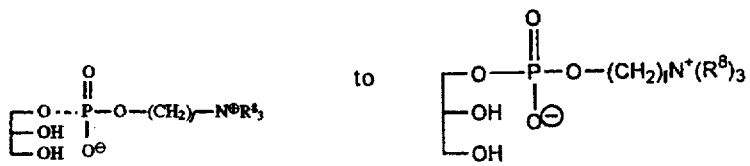

In Column 17, line 30, insert --atoms-- after "silicon".

In Column 17, lines 47 and 54 (in formulas), change "," to --r--.

In Column 18, lines 24 to 26 (in formulas), change "," to --r--.

In Column 18, lines 45 and 51 (in formula), change "$(CR^{18}_2)_sO]_o(CR^{18}_2)_sR^{18}$" to --$(CR^{18}_2)_nO]_o(CR^{18}_2)_nR^{18}$--.

In Column 18, line 54 (in formula), change "$(CR^{18}_2)_sO$" to --$(CR^{18}_2)_nO$--.

In Column 19, lines 2 and 3 (in formula), change "$[(CR^{18}_2)_sO]$" to --$[(CR^{18}_2)_nO]$--.

In Column 19, line 57, change "claims" to --chains--.

In Column 19, line 65, change "comoners" to --comonomers--.

In Column 20, line 54 (in formula), change "-(CH)$_q$c(O)O-" to -- -(CH$_2$)$_q$C(O)O- --.

In Column 20, line 55 (in formula), delete "13".

In Column 21, line 44, change "-(CR$^{22}_2$),-" to -- -(CR$^{22}_2$)$_r$- --.

In Column 22, lines 2 to 7 (in diagram), join $K^2$ and the closest apex of the styrene ring with a line.

In Column 22, line 33, change "of" to --or--.

In Column 22, line 57, change "(Het)" to --Het--.

UNITED STATES PATENT AND TRADEMARK OFFICE
CERTIFICATE OF CORRECTION

PATENT NO. : 5,783,650
DATED : July 21, 1998
INVENTOR(S) : RODERICK W.J. BOWERS, STEPHEN A. JONES, PETER W. STRATFORD AND STEPENS A. CHARLES It is certified that error appears in the above-identified patent and that said Letters Patent is hereby corrected as shown below:

In Column 24, line 30, change "-(CH)$_x$C(O)O-" to -- -(CH$_2$)$_x$C(O)O- --.
In Column 25, line 33, change "from" to --form--.
In Column 26, line 64, delete "containing a group".
Claim 1, Column 50, line 46 (in formula), change "-(CH),C(O))-" to -- -(CH$_2$)$_x$C(O)- --. 
Claim 1, Column 50, line 48, change "$^x$C(O)NR$^{28}$-" to --$_x$C(O)NR$^{28}$- --.
Claim 8, Column 53, line 14 (in formula), change "-(CH)$_x$C(O))-" to -- -(CH$_2$)$_x$C(0)- --.
Claim 9, Column 53, lines 34 to 37 (in diagram) change

Signed and Sealed this

Twenty-third Day of March, 1999

Attest:

Q. TODD DICKINSON

Attesting Officer

Acting Commissioner of Patents and Trademarks